(12) United States Patent
Lamego et al.

(10) Patent No.: US 10,729,335 B2
(45) Date of Patent: Aug. 4, 2020

(54) HANDHELD PROCESSING DEVICE INCLUDING MEDICAL APPLICATIONS FOR MINIMALLY AND NON INVASIVE GLUCOSE MEASUREMENTS

(71) Applicant: Cercacor Laboratories, Inc., Irvine, CA (US)

(72) Inventors: Marcelo M. Lamego, Cupertino, CA (US); Massi Joe E. Kiani, Laguna Niguel, CA (US); Jeroen Poeze, Rancho Santa Margarita, CA (US); Cristiano Dalvi, Lake Forest, CA (US); Sean Merritt, Lake Forest, CA (US); Hung Vo, Fountain Valley, CA (US); Gregory A. Olsen, Trabuco Canyon, CA (US); Ferdyan Lesmana, Irvine, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

(21) Appl. No.: 16/230,734

(22) Filed: Dec. 21, 2018

(65) Prior Publication Data
US 2019/0142283 A1 May 16, 2019

Related U.S. Application Data

(63) Continuation of application No. 14/703,816, filed on May 4, 2015, now Pat. No. 10,159,412, which is a (Continued)

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/0022* (2013.01); *A61B 5/1455* (2013.01);
(Continued)

(58) Field of Classification Search
CPC . A61B 5/0002; A61B 5/1455; A61B 5/14551; A61B 5/14532; A61B 5/0205;
(Continued)

(56) References Cited

U.S. PATENT DOCUMENTS 3,316,395 A  4/1967 Lavin
3,316,396 A  4/1967 Lavin
(Continued)

OTHER PUBLICATIONS

PCT/ISA/206 and Annex to Form PCT/ISA/2006 Communication Relating to the Results of the Partial International Search dated Mar. 23, 2012, in 7 pages.

*Primary Examiner* — Eric F Winakur
*Assistant Examiner* — Chu Chuan Liu
(74) *Attorney, Agent, or Firm* — Knobbe Martens Olson & Bear LLP

(57) ABSTRACT

The present disclosure includes a handheld processing device including medical applications for minimally and noninvasive glucose measurements. In an embodiment, the device creates a patient specific calibration using a measurement protocol of minimally invasive measurements and noninvasive measurements, eventually creating a patient specific noninvasive glucometer. Additionally, embodiments of the present disclosure provide for the processing device to execute medical applications and non-medical applications.

16 Claims, 26 Drawing Sheets

Related U.S. Application Data continuation of application No. 13/308,461, filed on Nov. 30, 2011, now abandoned.

(60) Provisional application No. 61/418,807, filed on Dec. 1, 2010, provisional application No. 61/422,284, filed on Dec. 13, 2010.

(51) Int. Cl.
  *A61B 5/145*    (2006.01)
  *A61B 5/1455*   (2006.01)
  *A61B 5/1459*   (2006.01)
  *A61B 5/021*    (2006.01)
  *A61B 5/08*     (2006.01)

(52) U.S. Cl.
  CPC ........ *A61B 5/1459* (2013.01); *A61B 5/14532* (2013.01); *A61B 5/7435* (2013.01); *A61B 5/7475* (2013.01); *A61B 5/021* (2013.01); *A61B 5/0816* (2013.01); *A61B 5/14546* (2013.01); *A61B 2560/0223* (2013.01); *A61B 2560/0431* (2013.01)

(58) Field of Classification Search
  CPC ... A61B 5/7475; A61B 5/0022; A61B 5/7435; A61B 5/1459; A61B 5/021; A61B 5/14546; A61B 5/0816
  See application file for complete search history.

(56) References Cited

U.S. PATENT DOCUMENTS

| | | |
|---|---|---|
| 4,163,290 A | 7/1979 | Sutherlin et al. |
| 4,305,059 A | 12/1981 | Benton |
| 4,491,725 A | 1/1985 | Pritchard |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,507,288 A | 4/1996 | Bocker et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Nader et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,830,137 A * | 11/1998 | Scharf ................ A61B 5/14551 600/323 |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,945,676 A | 8/1999 | Khalil et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,047 B1 | 5/2001 | Malin et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,405,065 B1 | 6/2002 | Malin et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |

(56) References Cited

U.S. PATENT DOCUMENTS

| | | |
|---|---|---|
| 6,442,408 B1 | 8/2002 | Wenzel et al. |
| 6,456,870 B1 | 9/2002 | Rennert et al. |
| 6,463,311 B1 | 10/2002 | Diab |
| 6,470,199 B1 | 10/2002 | Kopotic et al. |
| 6,475,800 B1 | 11/2002 | Hazen et al. |
| 6,487,429 B2 | 11/2002 | Hockersmith et al. |
| 6,493,566 B1 | 12/2002 | Ruchti et al. |
| 6,501,975 B2 | 12/2002 | Diab et al. |
| 6,501,982 B1 | 12/2002 | Ruchti et al. |
| 6,505,059 B1 | 1/2003 | Kollias et al. |
| 6,512,936 B1 | 1/2003 | Monfre et al. |
| 6,512,937 B2 | 1/2003 | Blank et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,587,702 B1 | 7/2003 | Ruchti et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,668,181 B2 | 12/2003 | Wenzel et al. |
| 6,671,531 B2 | 12/2003 | Al-Ali et al. |
| 6,671,542 B2 | 12/2003 | Rennert et al. |
| 6,675,029 B2 | 1/2004 | Monfre et al. |
| 6,678,543 B2 | 1/2004 | Diab et al. |
| 6,684,090 B2 | 1/2004 | Ali et al. |
| 6,684,091 B2 | 1/2004 | Parker |
| 6,697,654 B2 | 2/2004 | Lorenz et al. |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,777,240 B2 | 8/2004 | Hazen et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,584 B2 | 1/2005 | Makarewicz et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,864,978 B1 | 3/2005 | Hazen et al. |
| 6,871,169 B1 | 3/2005 | Hazen et al. |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,010,336 B2 | 3/2006 | Lorenz et al. |
| 7,015,451 B2 | 3/2006 | Dalke et al. |
| 7,015,782 B2 | 3/2006 | Kincaid et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,038,774 B2 | 5/2006 | Hazen et al. |
| 7,039,446 B2 | 5/2006 | Ruchti et al. |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,183,102 B2 | 2/2007 | Monfre et al. |
| 7,186,966 B2 | 3/2007 | Al-Ali |
| 7,190,261 B2 | 3/2007 | Al-Ali |
| 7,206,623 B2 | 4/2007 | Blank et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,233,816 B2 | 6/2007 | Blank et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,080 B2 | 11/2007 | Acosta et al. |
| 7,317,938 B2 | 1/2008 | Lorenz et al. |
| 7,328,053 B1 | 2/2008 | Diab et al. |
| 7,332,784 B2 | 2/2008 | Mills et al. |
| 7,333,843 B2 | 2/2008 | Monfre et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |

(56) References Cited

U.S. PATENT DOCUMENTS

| | | |
|---|---|---|
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,789 C1 | 5/2008 | Liu |
| 7,377,794 B2 | 5/2008 | Al Ali et al. |
| 7,377,899 B2 | 5/2008 | Weber et al. |
| 7,383,069 B2 | 6/2008 | Ruchti et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,436,511 B2 | 10/2008 | Ruchti et al. |
| 7,438,683 B2 | 10/2008 | Al-Ali et al. |
| 7,440,786 B2 | 10/2008 | Hockersmith et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,505,801 B2 | 3/2009 | Monfre et al. |
| 7,509,153 B2 | 3/2009 | Blank et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| 7,729,733 B2 | 6/2010 | Al-Ali et al. |
| 7,734,320 B2 | 6/2010 | Al-Ali |
| 7,751,192 B2 | 7/2010 | Abul-Haj et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,772,612 B2 | 8/2010 | Wojtczuk et al. |
| 7,787,924 B2 | 8/2010 | Acosta et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,955,965 B2 | 6/2011 | Wojtczuk et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 7,993,005 B2 | 8/2011 | MacIntyre et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,242,009 B2 | 8/2012 | Wojtczuk et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,324,578 B2 | 12/2012 | Dinh et al. |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |

(56) References Cited

U.S. PATENT DOCUMENTS

| | | |
|---|---|---|
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,447,374 B2 | 5/2013 | Diab |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |

(56) References Cited

U.S. PATENT DOCUMENTS

| | | |
|---|---|---|
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B2 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 2002/0133068 A1* | 9/2002 | Huiku ............... A61B 5/14551 600/331 |
| 2003/0181798 A1* | 9/2003 | Al-Ali ............... A61B 5/02438 600/324 |
| 2004/0102687 A1* | 5/2004 | Brashears ............ A61B 5/0002 600/323 |
| 2004/0133086 A1 | 7/2004 | Ciurezak et al. |
| 2005/0107676 A1 | 5/2005 | Acosta et al. |
| 2006/0161054 A1 | 7/2006 | Reuss et al. |
| 2007/0282478 A1 | 12/2007 | Al-Ali et al. |

(56) References Cited

U.S. PATENT DOCUMENTS

| | | |
|---|---|---|
| 2008/0076972 A1 | 3/2008 | Dorogusker et al. |
| 2009/0270755 A1* | 10/2009 | Czerwinski ........... A61B 5/1118 600/545 |
| 2009/0275813 A1 | 11/2009 | Davis |
| 2010/0056877 A1* | 3/2010 | Fein ........................ A61B 8/06 600/301 |
| 2011/0082711 A1 | 4/2011 | Poeze et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0253334 A1 | 9/2013 | Al-Ali et al. |
| 2013/0296672 A1 | 11/2013 | O'Neil et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0275835 A1 | 9/2014 | Lamego et al. |
| 2014/0275871 A1 | 9/2014 | Lamego et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0357966 A1 | 12/2014 | Al-Ali et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0094546 A1 | 4/2015 | Al-Ali |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0014083 A1 | 1/2017 | Diab et al. |
| 2017/0014084 A1 | 1/2017 | Al-Ali et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |

(56) References Cited

U.S. PATENT DOCUMENTS

| | | |
|---|---|---|
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |

\* cited by examiner

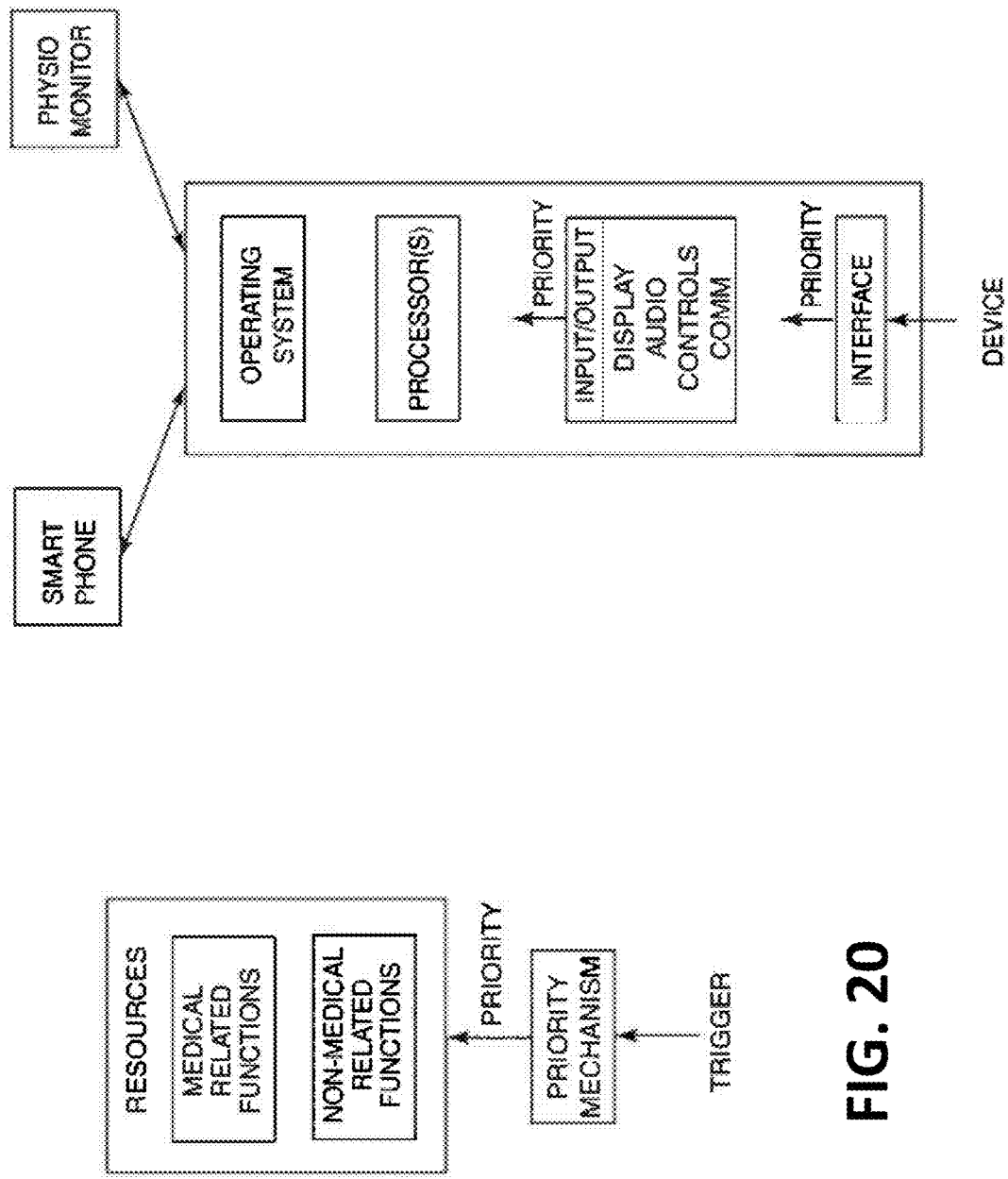

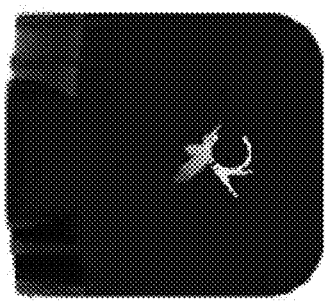
BATTERY CARTRIDGE
CO parts/mil CARTRIDGE
TEMP AND BP CARTRIDGE
GLUCOSE SENSOR CARTRIDGE
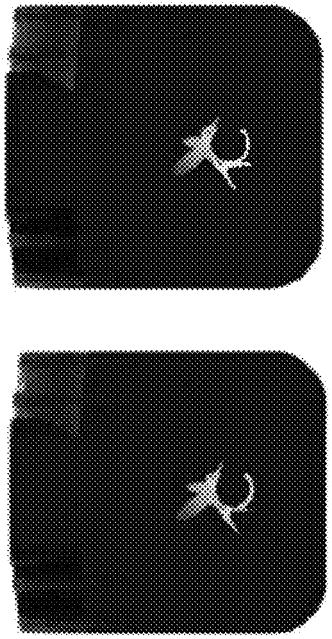
GLUCOSE SENSOR CABLE CARTRIDGE
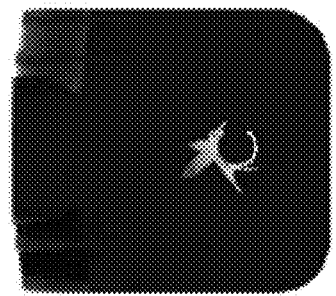
OXIMETRY SENSOR CARTRIDGE
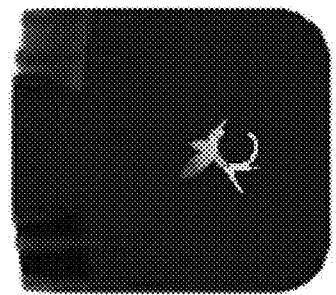
COOXIMETRY SENSOR CARTRIDGE
SCANNER/PATIENT INFO CARTRIDGE
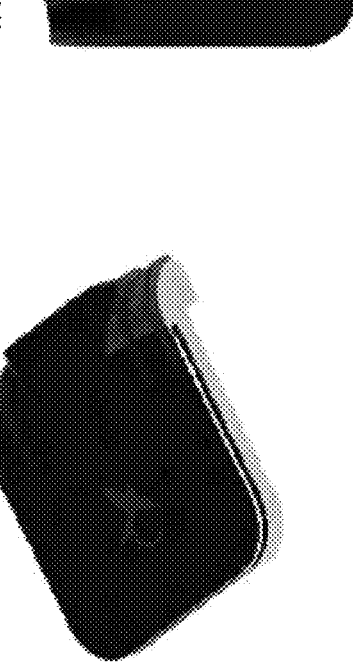
FIG. 31

HANDHELD PROCESSING DEVICE INCLUDING MEDICAL APPLICATIONS FOR MINIMALLY AND NON INVASIVE GLUCOSE MEASUREMENTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The present application relates to the field of physiological monitoring devices. Specifically, the present application relates to the field of glucometers.

BACKGROUND OF THE DISCLOSURE

Medical device manufacturers are continually increasing the processing capabilities of patient monitors, specifically of patient monitors that process signals based on attenuation of light by patient tissue. In general, such patient monitoring systems include one or more optical sensors that irradiate tissue of a patient and one or more photodetectors that detect the radiation after attenuation thereof by the tissue. The sensor communicates the detected signal to a patient monitor, where the monitor often removes noise and preprocesses the signal. Advanced signal processors then perform time domain and/or frequency domain processing to determine measurements of blood constituents and other physiological parameters of the patient.

Manufacturers have advanced basic pulse oximeters that determine measurements for blood oxygen saturation ("SpO2"), pulse rate ("PR") and pethysmographic information, to read-through-motion oximeters, to co-oximeters that determine measurements of many constituents of circulating blood. For example, Masimo Corporation of Irvine Calif. ("Masimo") manufactures pulse oximetry systems including Masimo SET® low noise optical sensors and read through motion pulse oximetry monitors for measuring Sp02, PR, perfusion index ("PI") and others. Masimo sensors include any of LNOP®, LNCS®, SofTouch™ and Blue™ adhesive or reusable sensors. Masimo oximetry monitors include any of Rad-8®, Rad-5®, Rad®-5v or SatShare® monitors.

Many innovations improving the measurement of blood constituents are described in at least U.S. Pat. Nos. 6,770,028; 6,658,276; 6,157,850; 6,002,952; 5,769,785 and 5,758,644, which are assigned to Masimo and are incorporated by reference herein. Corresponding low noise optical sensors are disclosed in at least U.S. Pat. Nos. 6,985,764; 6,088,607; 5,782,757 and 5,638,818, assigned to Masimo and incorporated by reference herein.

Masimo also manufactures more advanced co-oximeters including Masimo Rainbow® SET, which provides measurements in addition to Sp02, such as total hemoglobin (SpHb™), oxygen content (SpCO™), methemoglobin (SpMet®), carboxyhemoglobin (SpCO®) and PVI®. Advanced blood parameter sensors include Masimo Rainbow® adhesive, ReSposable™ and reusable sensors. Masimo's advanced blood parameter monitors include Masimo Radical-7™, Rad-87™, and Rad-57™ monitors as well as Pronto and Pronto-7 spot check monitors.

Innovations relating to these more advanced blood parameter measurement systems are described in at least U.S. Pat. Nos. 7,647,083; 7,729,733; U.S. Pat. Pub. Nos. 2006/0211925; and 2006/0238358, assigned to Cercacor Laboratories of Irvine, Calif. ("Cercacor") and incorporated by reference herein.

Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY OF THE DISCLOSURE

The present disclosure includes a handheld processing device including medical applications for minimally and noninvasive glucose measurements. In an embodiment, the device includes a minimally invasive glucose biosensor ("strip reader"). Manufacturers have developed strip readers in various embodiments for decades primarily for the measurement of glucose. Such strip readers often employ disposable strips that include an enzyme electrode and mediator compound, where the mediator compound moves electrons between the enzyme and the electrode to result in a measurable electrical current at the electrode when glucose is present. The strip reader measures this current when the disposable strip is inserted and then determines glucose values corresponding to the received current. Diabetics, for example, often rely on strip readers to provide minimally invasive measurements of their glucose levels. In short, a user often pricks a finger and deposits one or more droplets of blood on a test strip. The user then inserts the blood carrying strip into a strip reader, which in turn uses the measurable electrical signal to determine glucose measurements for the user.

In an embodiment, the device also includes a noninvasive glucose measurement solution. For example, the device communicates with a noninvasive optical sensor to receive signals responsive to the attenuation of various wavelengths of light by a user's tissue. The device processes these signals to determine current glucose measurements for the user.

As is widely understood by one of ordinary skill in the glucose measurement arts, noninvasive determination of glucose through processing absorption signals is complicated and often difficult to accurately perform over large patient populations. In an embodiment of the present disclosure, patient specific calibration of the device occurs through information exchanges between the device, with its the minimally invasive and noninvasive measurements, and a centralized computing system. For example, the device communicates with one or more remote computing centers to upload patient measurements and download, for example, patient specific calibrations. Through the interaction of the centralized computing system and many processing devices as disclosed herein, the manufacturer collects vast amounts of anonymous physiological data associating minimally invasive measurements and noninvasive measurements. These associations can then produce reliable calibration data specific to a user and across large user populations. For example, in certain embodiments, uploads of thousands to hundreds of thousands of measurements per week create data resources unobtainable through traditional clinical testing environments.

Additional embodiments of the present disclosure include the processing device including medical related functions and non-medical related functions that may share common resources. Advantageously, the processing device includes a priority mechanism so as to prevent the medical related functions from competing with the non-medical related functions for the common resources during critical time periods. These critical time periods may be indicated by triggering events. In particular, a triggering event indicates to the system that the medical related functions have resource priority. This priority may be, for example, exclusive access to and use of displays, alarms, controls, communications and processing power so as to make time critical patient health and risk assessments and output those assessments in a timely manner to a healthcare provider. In an embodiment, the physiological monitor is integrated with a smart phone so as to advantageously allow flexible communications between the physiological monitor and a broad range of external information sources and information receivers. These communications occur over any of a wide variety of communication links, both wired and wireless. Wireless communications may include, but are not limited to, GPS, cellular networks, Wi-Fi and Bluetooth to name a few, so as to connect to the Internet, telephone systems and other wide area networks. Wired communications may include, but are not limited to, USB. A broad range of third-party applications are available for the smart phone, also providing increased functionality to the physiological monitor.

In additional embodiments, the processing device may include the alteration of smart phone processing systems to manage physiological data. For example, in some embodiments, a processing board or card may be included within an existing smart phone technology. The board or card may include one or more signal processors and associated memory, I/O, and the like to provide measurement or other physiological data to applications executing on traditional smart phone processing environments. In an embodiment, the communication may be wired or wireless and the board or card may be internal or external. In some cases, the board may be a clip-on cartridge or other smart phone extension that electronically and/or physically mates with the housing and processing of the smart phone.

In an embodiment, a monitoring board may be physically integrated and attach to a connected sensor. In another embodiment, the monitoring board may mechanically and/or electrically mate with the smart phone. In this embodiment, the sensor may include the monitoring board, which then communicates with a smart phone, or portions of the monitoring board may be shared between an external sensor and the smart phone. In a standalone embodiment, the monitoring board and the sensor may be an integrated unit or a unit with an attached sensor, where the unit communicates with smart phone or other digital processing devices.

For purposes of summarizing the invention, certain aspects, advantages and novel features of the invention have been described herein. Of course, it is to be understood that not necessarily all such aspects, advantages or features will be embodied in any particular embodiment of the invention.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

The following drawings and the associated descriptions are provided to illustrate embodiments of the present disclosure and do not limit the scope of the claims.

FIGS. 10-19 illustrate exemplary user interfaces of the processing device of FIG. 1, according to various embodiments of the present disclosure. Specifically, FIG. 10 illustrates an exemplary test result interface, FIG. 11 illustrates an exemplary bar graph interface, FIG. 17 illustrates an exemplary applications interface.

FIG. 20 illustrates a simplified block diagram of a priority mode processing device according to an embodiment of the present disclosure.

FIG. 21 illustrates a simplified block diagram of a priority mode processing device according to an embodiment of the present disclosure.

FIG. 31 illustrates various exemplary connectable cartridges for an expanded smart phone to provide medical processing capabilities, according to an embodiment of the disclosure.

DETAILED DESCRIPTION OF THE PREFERRED EMBODIMENTS

The present disclosure includes a handheld processing device including medical applications for minimally and noninvasive glucose measurements. In an embodiment, the device creates a patient specific calibration using a measurement protocol of minimally invasive measurements and noninvasive measurements, eventually creating a patient specific calibrated noninvasive glucometer. Additionally, embodiments of the present disclosure provide for the processing device to execute medical applications and non-medical applications. In an embodiment the medical applications may advantageously relate to the foregoing patient specific noninvasive glucometer. Such applications may advantageously include measurement applications, tracking applications including diet applications to track caloric intake and/or caloric usages, calendaring, and other glucose management applications. In other embodiments, other medical applications may monitor respiration, blood pressure, other blood parameters, combinations of parameters, wellness measurements or the like. The nonmedical applications may include communication protocols, connectivity protocols, smart phone and cellphone capabilities, entertainment applications, productivity applications, or virtually any application available on today's existing sophisticated smart phones.

In other embodiment's, the processing device generates patient specific calibrations through information exchanges between the device and a centralized computing system. For example, the device may upload measurement information to one or more remote computing data centers over wireless, mobile, Wi-Fi, wired, or other networks and download patient specific or other updated calibrations. Advantageously, through the upload of measurement data, the manufacturer may collect anonymous clinical data that can be used to create ever more accurate noninvasive measurements.

According to further embodiments, the processing device includes medical and nonmedical applications that may share common resources. Advantageously, the processing device includes a priority mechanism so as to prevent the medical related functions from competing with the non-medical related functions for the common resources during critical or otherwise medically relevant time periods.

In still further embodiments of the present disclosure, such processing devices as disclosed herein may be incorporated into existing smart phone processing platforms.

To facilitate a complete understanding of the invention, the remainder of the detailed description describes the invention with reference to the drawings, wherein like reference numbers are referenced with like numerals throughout.

Figure 1:
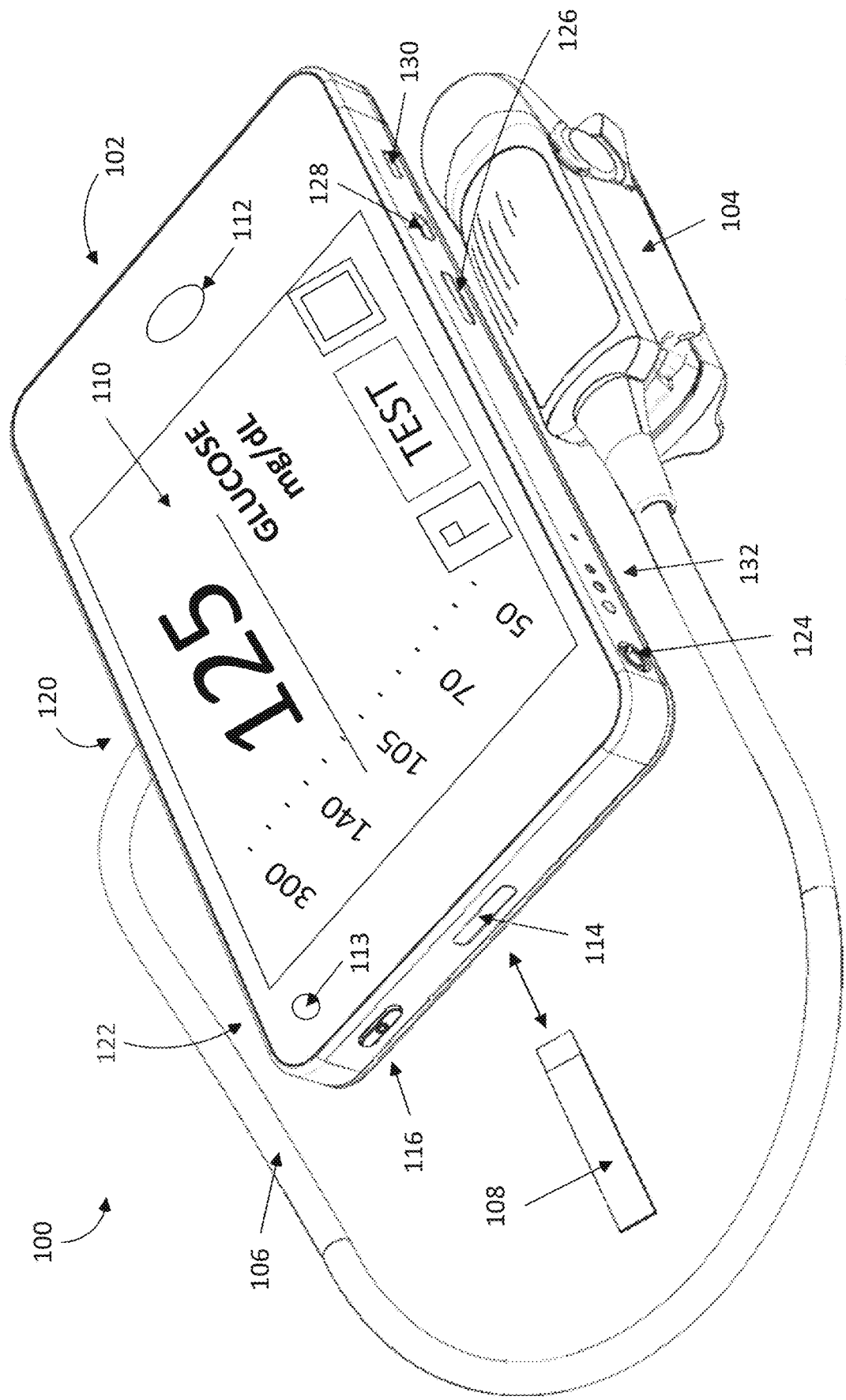
FIG. 1 illustrates a simplified perspective view of a processing system according to an embodiment of present disclosure, including a processing device, a noninvasive sensor, a cable providing communication between the device and the sensor, and a disposable strip.
Figure 2:
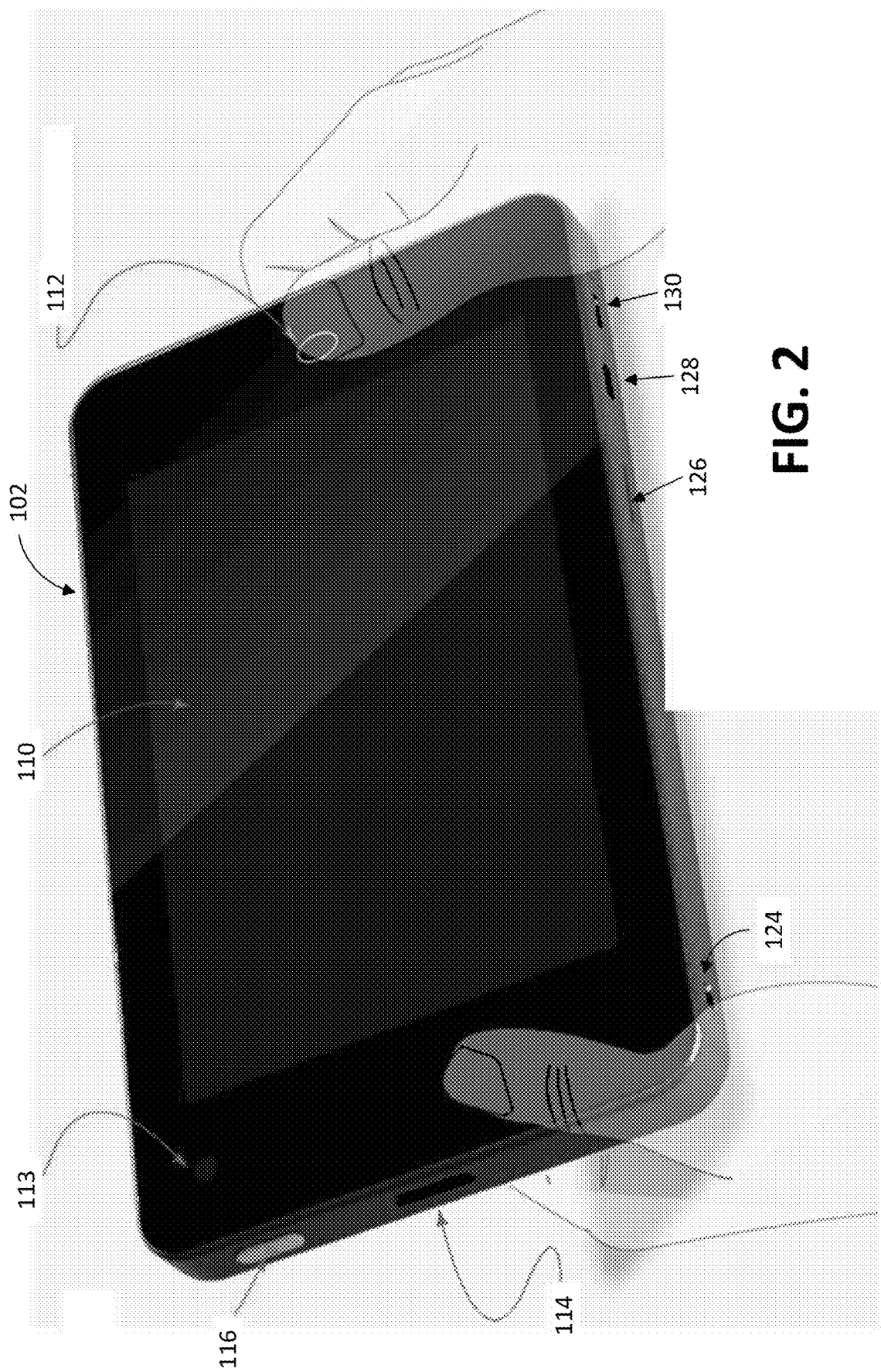
FIG. 2 illustrates a simplified perspective view of the processing device of FIG. 1, according to an embodiment of present disclosure.

FIG. 1 illustrates a simplified perspective view of a processing system 100 according to an embodiment of present disclosure, including a processing device 102, a noninvasive sensor 104, an associated cable 106 providing communication between the device 102 and the sensor 104, and a disposable glucose strip 108. The processing device 100 comprises a handheld housing including an integrated touch screen 110, one or more input keys 112, and an integrated camera 113 preferably capable of photo and/or video capture. In an embodiment, the screen 110 rotates as the device 102 is held in differing orientations; however, the preferred orientation is for use is the landscape orientation as illustrated in FIG. 2.

Figure 3:
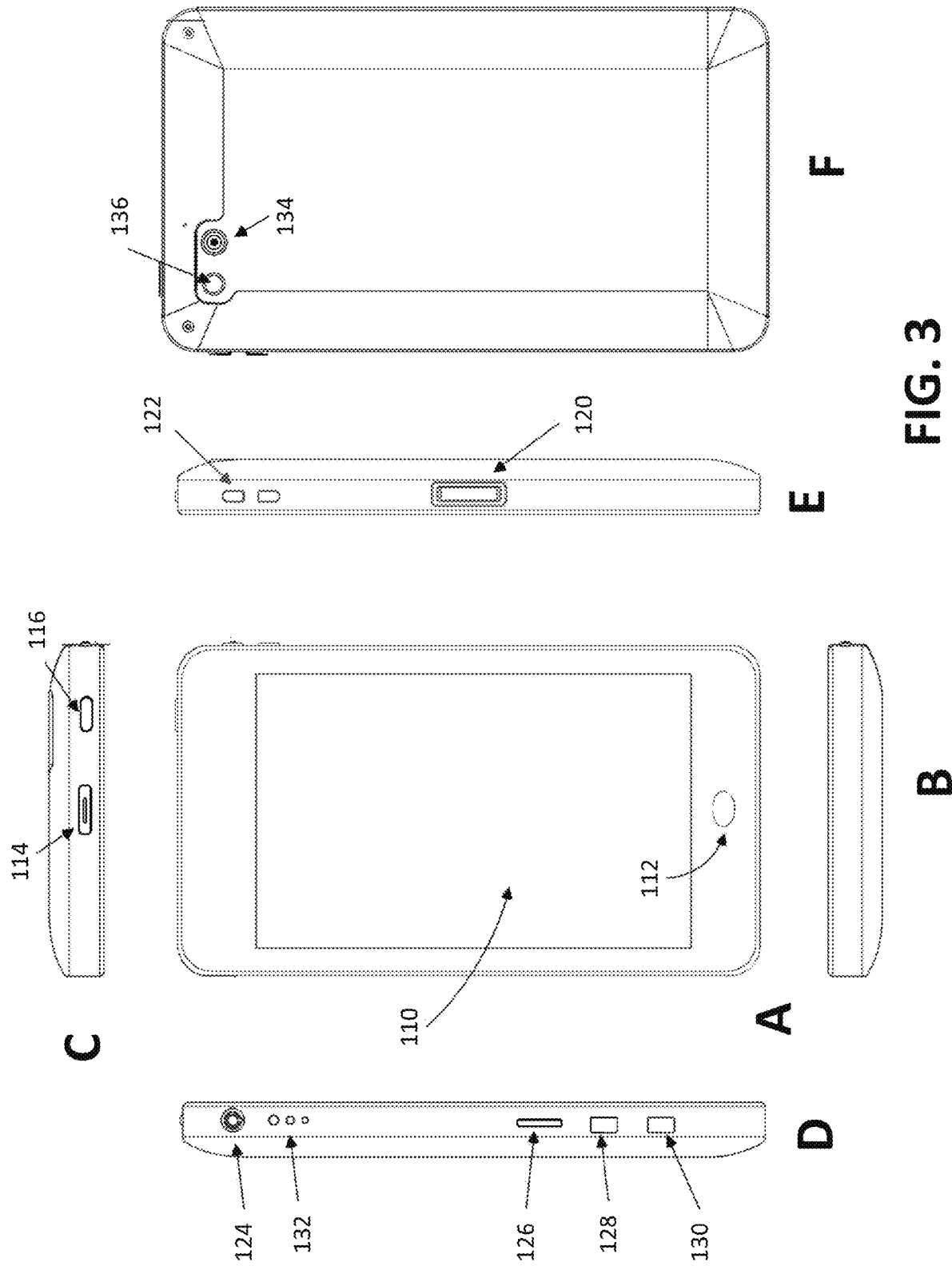
FIGS. 3A-3F illustrate simplified top, front, rear, left, right, and back views of the processing device of FIG. 1, according to an embodiment of present disclosure.

FIG. 1 also illustrates additional features of the device 102. For example, the device 102 includes along a side thereof an integrated strip reader, including a strip input cavity 114, and a power button 116. Along another side, the device 102 includes a noninvasive sensor cable input port 120 (FIG. 3E) and volume controls 122 (FIG. 3E). Along yet another side, the device 102 includes a headphone jack 124, a micro SD card reader input cavity 126, a micro HDMI connector 128, a Micro USB connector 130 configured for, for example, data transfer and battery charging, and an optional audio transducer, such as, for example, a speaker 132. Along a back side thereof, in an embodiment, the processing device 102 includes a camera 134 (FIG. 3F) and LED flash 136 (FIG. 3F).

As disclosed, the device 102 communicates with a noninvasive optical sensor 104, such as, for example, a clothes-pin style reusable optical sensor, in some mechanical respects similar to those employed in standard pulse oximetry. The sensor 104 may also include advanced features, such as those disclosed in U.S. Pat. No. 6,580,086, and U.S. Pat. Pub. No. 2010-0026995, on Feb. 4, 2010, titled "Multi-stream Sensor For Noninvasive Measurement of Blood Constituents," each of which is incorporated by reference herein. Specifically, the sensor 104 includes a plurality of emitters emitting light of a variety of wavelengths to form a light source. A plurality of detectors detect the light after attenuation by a digit of the patient. A plurality of temperature sensors and one or more memory devices may also be incorporated into the sensor 104. These devices communicate their information to the device 102 through the cable 106.

In general, the user interacts with the processing device 102 to obtain glucose measurements. The user may input the disposable strip 108 with a blood sample and the device 102 will, if not already, electronically wake up a medical application and display glucose measurements obtained from the strip reader. The user may also apply the sensor 104 to a digit and upon activating a "test" input, the device 102 may process the detector signals and display glucose measurements derived from the received signals.

Although disclosed with respect to the embodiment shown in FIG. 1, an artisan will recognize from the disclosure herein alternative or additional functionality, user interaction mechanisms, and the like. For example, the device housing may be shaped to ergonomically fit a user's hand, may include more or less input mechanisms including, for example, a connectable or slideout keyboard, a pointing device, speech recognition applications, or the like. Moreover, the sensor 104 may wirelessly communicate with the device 102. The device 102 may communicate with an external strip reader or other medical sensors or devices.

FIGS. 3A-3F illustrate simplified top, front, rear, left, right, and back views of the processing device 102 of FIG. 1, according to an embodiment of present disclosure.

Figure 4:
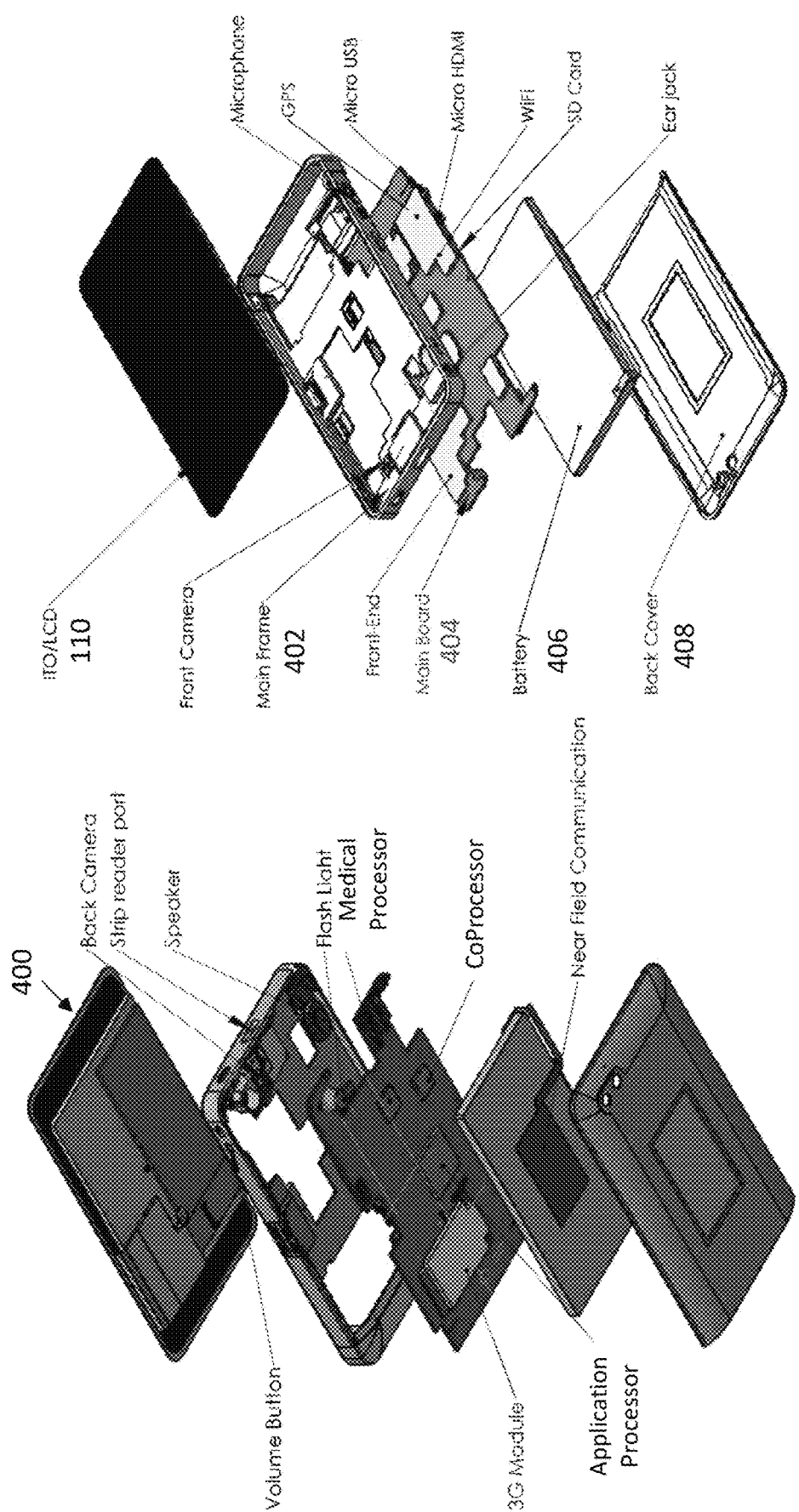
FIGS. 4A-4B illustrate simplified exploded views of the processing device of FIG. 1, according to an embodiment of present disclosure.

FIGS. 4A-4B illustrate simplified exploded views of the processing device 102 of FIG. 1, according to an embodiment of present disclosure. As shown, the device 102 includes the touch screen 110 housed in an upper housing 400, a main frame 402, a main board 404, a battery 406 and a rear housing or casing 408. In an embodiment, the touch screen 110 comprises a 5.6" LED backlit LCD with 1280× 800 pixel resolution with 262,144 colors and a viewing angle of 179 degrees, although an artisan will recognize from the disclosure herein a wide variety of possible display devices.

Figure 5:
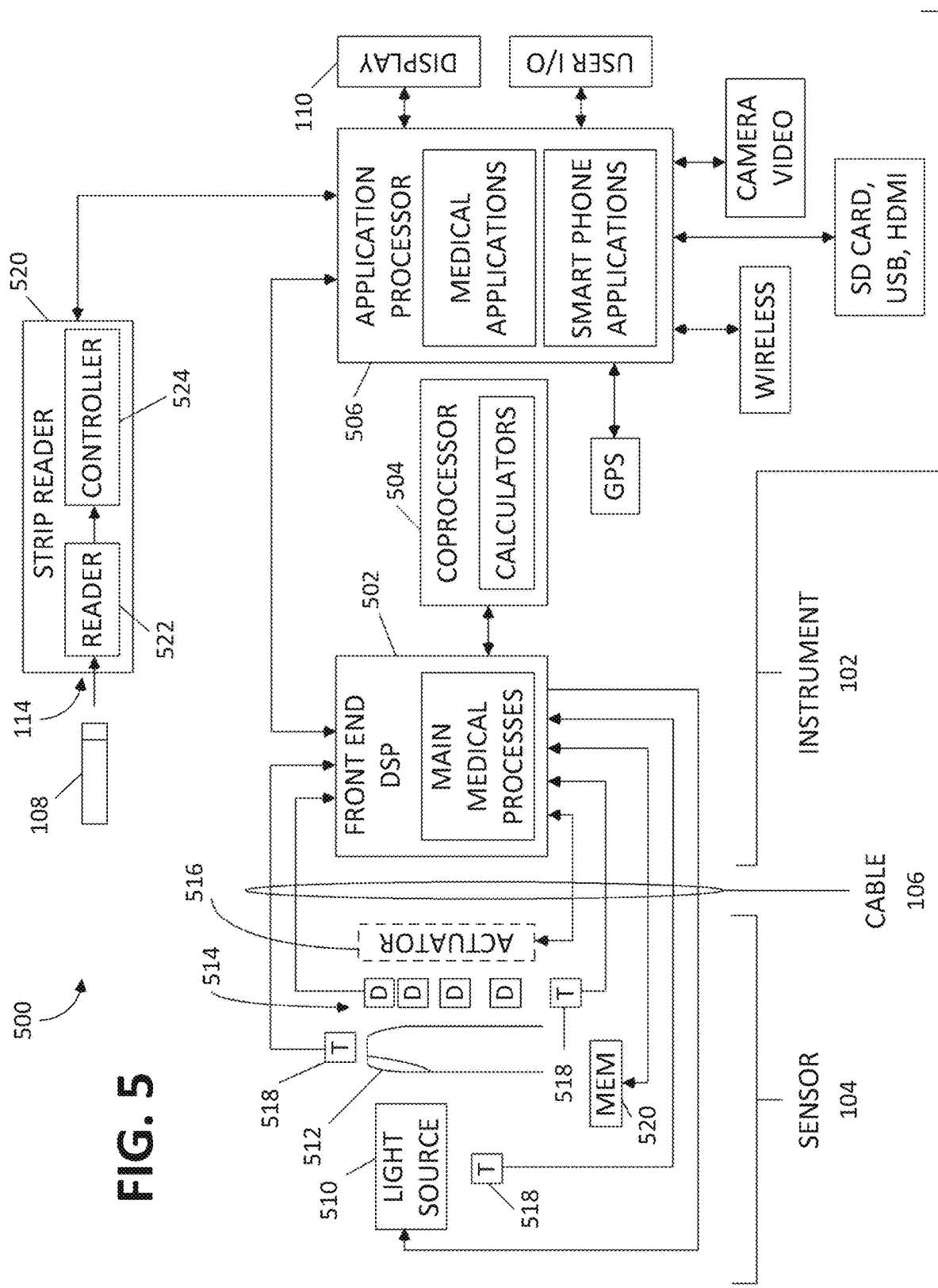
FIG. 5 illustrates a simplified hardware/software block diagram of the processing system of FIG. 1, according to an embodiment of present disclosure.

FIG. 5 illustrates a simplified hardware block diagram 500 of the processing system 100 of FIG. 1, according to an embodiment of present disclosure. As shown in FIG. 5, the processing device 102 includes a plurality of processors, including a front end processor 502 configured to execute a number of processes, including medical processes and signal processing processes, a coprocessing DSP 504 configured to execute a number of calculators and assist the front end 502 in intensive calculation processes, and an applications processor 506, configured to execute a medical applications and more traditional smart phone applications, including, for example, cell phone, internet, entertainment, and productivity applications. In an embodiment, the front end 502 comprises an OMAP style processing system available from Texas Instruments, generally comprising an ARM9 processor and one or more digital signal processors or specialized co-processors. In an embodiment, the front end 502 may comprise an OMAP L138 processor system. In an embodiment, the coprocessor 504 comprises a Snowbird style digital signal coprocessor from Analog Devices. In an embodiment, the applications processor 506 comprises a Linux processor from Samsung including a Cortex-A9 ARM processor.

Although disclosed with reference to specific processing technologies, an artisan will recognize from the disclosure herein that the processor could comprises a single processing device, more or less than three (3) processing devices, a wide variety of hardware and/or software solutions, other processing devices, or the like.

The front end 502 communicates with the sensor 104 components to accomplish the noninvasive measurements of the present disclosure. For example, the front end 502 communicates with one or more light sources 510 to irradiate a digit 512 of a wearer of the sensor 104. A plurality of photodetectors 514 receive the irradiated light after attenuation by the tissue of the digit 512. In an embodiment, the detectors 514 comprises four (4) detectors logarithmically spaced apart along an axis parallel to a long axis of the digit 512, the detectors 514 optionally mounted on an actuator 516. In an embodiment, the actuator 516 moves the detectors in a predefined motion to create an active pulse technology, similar to that disclosed in U.S. Pat. No. 5,638,816, titled "Active Pulse Blood Constituent Monitoring," or in U.S. Pat. Prov. App. Ser. No. 61/486,689 filed on May 16, 2011, titled "Personal Health Device," each of which is incorporated by reference herein. The detectors 514 output their respective channels of data, or signals to the front end 502 for processing. In addition to the light source 510 and the detectors 514, the front end 502 may advantageously communicate with a plurality of temperature sensors 518, and one or more memories 520. In an embodiment, the front end 502 communicates with a temperature sensor 518 configured to supply an indication of the temperatures of the emitting LEDs of the light source 510, a temperature sensor 518 configured to supply an indication of the temperature of the tissue being monitored, and a temperature sensor 518 configured to supply and indication of the temperature of the detectors 514.

The front end processor 502 also communicates extensively with the coprocessor 504 over, for example, a dedicated high speed connection. In an embodiment, the medical application algorithms and mathematics that generate noninvasive measurements may be regarded as highly sensitive information. Thus, the communication between the processors 502 and 504 may advantageously be encrypted to ensure their sensitivity is appropriately guarded.

The front end processor 502 additionally communicates with the applications processor 506. In an embodiment, determined measurement values are forwarded to the applications processor 506, where, for example, medical applications use the data to present information to the user on the display 110. The applications processor 506 also communicates with the strip reader 520. In an embodiment, the strip reader 520 comprises a commercially available OEM strip reader from, for example, Nova Medical. In an embodiment, the strip reader includes a current detector, or reader 522 and a controller 524 for determining from an inserted strip 108, minimally invasive glucose measurements. The reader 520 forwards calculated measurements to the applications processor 506, where, for example, medical applications use the data to present information to the user on the display 110.

As disclosed in the foregoing, the applications processor 506 executes a wide variety of medical applications and smart phone or other applications, any of which may access wireless communication functionality, including Wi-Fi, 3 and/or 4 G or higher connectivity, Bluetooth, Ant, near field communication ("NFC"), cellular, or other wireless connectivity, SD card functionality, HDMI functionality, image and video data, and user input.

Although disclosed with reference to the specific embodiment of FIG. 5, an artisan will recognize from the disclosure herein other hardware and/or software configurations for accomplishing the desired functionality, including, for example, custom semiconductors, controllers, processors, or the like for performing individual or sets of functions.

Figure 6:
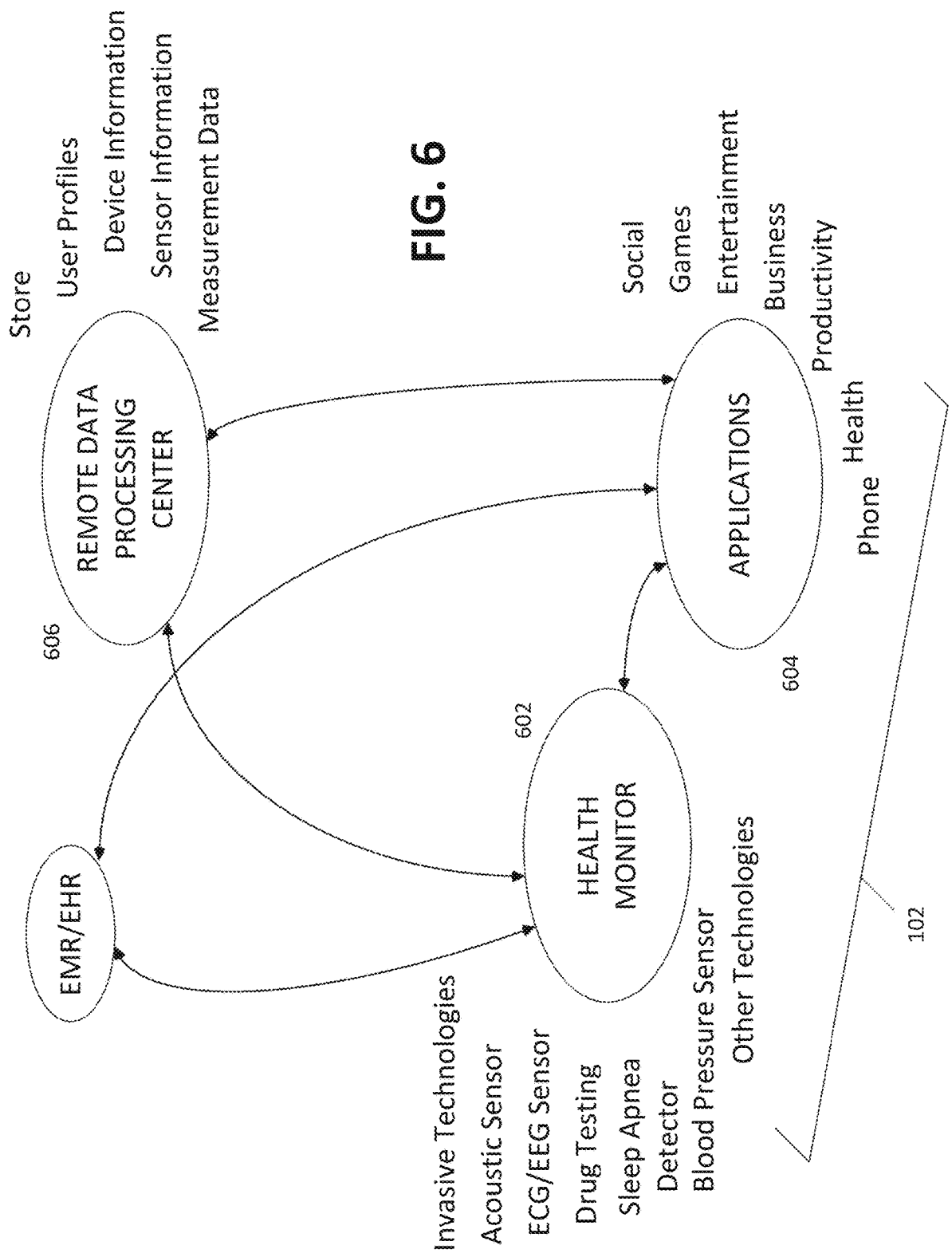
FIG. 6 illustrates a simplified data flow diagram between applications of the processing device of FIG. 1 and remote computing servers, according to an embodiment of present disclosure.

FIG. 6 illustrates a simplified data flow diagram between applications of the processing device 102 of FIG. 1 and remote computing servers, according to an embodiment of present disclosure. As shown in FIG. 6, a health monitor 602 including, for example, the glucometer as disclosed above, communicates data with a number of other processing centers, including a number of applications 604 and at least one remote data processing center 606. As shown in FIG. 6, the health monitor 602 may communicate with one or more of the following sensors, devices, or technologies: ECG and/or EEG sensors or devices, respiration sensors or devices, including acoustic sensors such as those commercially available from Masimo, sleep apnea sensors or monitors, invasive technologies such as the above discussed strip reader or other invasive technologies, blood pressure sensors or devices, temperature sensing technologies, drug testing sensors or devices, depth of consciousness sensors or devices, and other patient monitoring devices. As shown in FIG. 6, this interaction with the monitor 602 advantageously allows the monitor to use the information in its medical calculations, as well provide that information further to various applications 604 and the remote processing center 606.

The applications 604 may include a wide variety of applications including, for example, the health applications disclosed herein, or similar applications, phone, business, entertainment including video, music, pictures, and the like, productivity, social, games, utility applications and the like, many of which can be associated with today's smart phone technologies. In an embodiment, the applications may include some combination or all of the applications disclosed in U.S. Pat. App. Pub. No. 2011-0082711, filed on Apr. 7, 2011, titled, "Personal Digital Assistant or Organizer for Monitoring Glucose Levels," incorporated by reference herein.

The remote data processing center 606 communicates with the health monitor 602 and the applications 604 to store and process vast amounts of data, including for example, minimally and noninvasive glucose measurements for patient specific and population calibration processing, electronic medical records ("EMR") and electronic health records ("EHR"), or the like. In an embodiment, the remote data processing center 606 may also perform device management functions, including, for example, maintenance of software and firmware executing on the processing device 102, and measurement credit processing, such as the measurement credit processing disclosed in U.S. Pat. App. Pub. No. 2011-0172498, filed Jul. 14, 2011, titled "Spot Check Monitor Credit System," incorporated by reference herein disclosing, in general, embodiments for managing spot check pricing for medical instruments.

As will be understood by an artisan from the disclosure herein, the data processing center 606 may comprise one or many physical and/or logical locations, servers, systems, or the like, accessible by any of a large number of connectivity options. It may be geographically distributed, may have mirrored or backup sites, may be one or many processing device or the like.

Communication between the device 102 and the remote data processing center 606 advantageously benefits all parties. For example, the user by sharing their measurement data in a confidential and/or anonymous manner provides valuable data to, for example, the manufacturer. The amount of this data could be staggering when compared with the amount of data traditionally gathered during clinical trials. Supplementing actual clinical trial information with valuable uploaded information provides a cost effective and timewise practical solution to very costly clinical trial studies. In return, the user receives from the remote processing center patient specific calibration data ensuring the most accurate association of absorption-derived data and output measurement data. For example, oximeters and cooximeters use clinical data to map noninvasive measurement results to clinically-determined output measurements. This mapping is often referred to as "calibration." With the present disclosure, the clinical data is vastly supplemented with user data creating much more accurate calibrations, and specifically, user-specific calibrations. These calibrations are downloaded to the monitor 602.

For example, because of many challenges associated with the accurate noninvasive optical absorption-based glucose measurements, variability in calibrations between subjects can be high, in some cases too high for global calibrations to accurately support large user populations. Thus, in an embodiment of the present disclosure, the processing device 102 improves its calibration for a specific user through communication with the data processing center 606. In an embodiment, qualification for use of the device 102 to provide noninvasive glucose measurements is dependent upon the interaction with the data processing center 606. For example, FIG. 7 and its disclosure relates to a protocol for qualifying or preparing a processing device 102 for use noninvasively.

Figure 7:
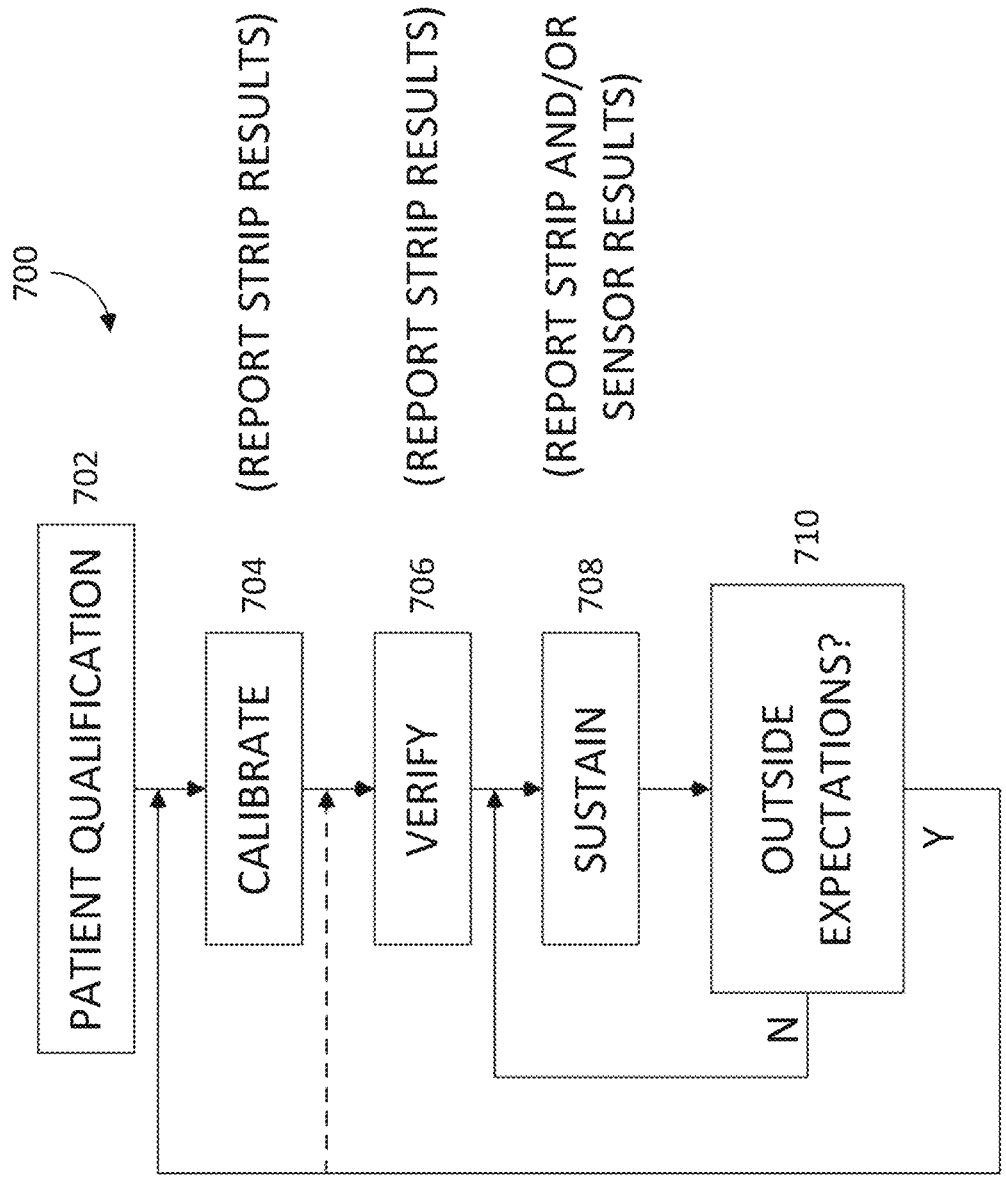
FIG. 7 illustrates a simplified measurement process according to an embodiment of the present disclosure.

FIG. 7 illustrates a simplified measurement process or protocol 700, according to an embodiment of the present disclosure. In an embodiment, the protocol 700 includes Step 702 where a patient qualifies for noninvasive glucose measurements. Some research suggests that only around seventy percent (70%) of possible patients qualify for noninvasive glucose measurements. Disqualification can be the result of many things, in particular optical density coupled with poor digit perfusion. Thus, in an embodiment, the device 102 may drive the light source 510 of the sensor 104 and receive optical absorption data. Based on the signal strength and/or quality of the data, the device 102 may request the user place the sensor on a different digit. Reasons for poor performance include finger thickness, pigmentation, perfusion, temperature, or the like. In some cases, the device 102 determines one or several ideal digits through the testing of each one for noninvasive measurements. In other embodiment, once the device 102 finds a sufficient digit, it recommends use of that one. Through, for example, the determination of potential signal strength of the optical signals received from the sensor 104, the device 102 may pre-qualify a user as a candidate for noninvasive glucose measurements. Full qualification may not occur at all or at least until much of the protocol 700 is completed.

The protocol 700 also includes Step 704, where the device 102 enters a calibration phase. During calibration, many invasive measurements, such as strip measurements are taken. In an embodiment, during this step, noninvasive measurements are not displayed as they are not sufficiently calibrated for a particular user. In an embodiment, about twenty (20) to about sixty (60) invasive measurements are performed during up to about thirty (30) days. In an embodiment, the user takes noninvasive measurements with each of the invasive measurements in order to associate instrument readings with invasive results. While providing a guideline for the calibration process, the protocol is not meant to be limited thereby. The device 102 uses a certain number of measurements over a certain time to develop a reliable calibration. Some users will enthusiastically provide multiple measurements, perhaps many measurements per day. Other will only provide a minimal number, such as one or two measurements per day. The calibration process length will be longer for the latter than it will for the former.

In an embodiment, because of the difficultly associated with cross subject variability in the calibrations process, e.g., the process of mapping noninvasive instrument readings with glucose values, in an embodiment, the device originates with a general calibration or in some cases, no calibration at all. The user begins taking measurements and uploads the measurements to the data processing center 606. After sufficient measurements, such as, for example, about twenty (20) to about one hundred (100) or so over about twenty (20) to forty five (45) days, the data processing center 606 will begin to see a convergence of the patient-specific calibration. In one sense, the mappings will begin to stabilize. For example, over that time period it is anticipated that the about minimums and about maximums start to fill in with patient specific correlations between noninvasive measurements and invasive measurements and the mapping functions will start to look more similar to the previous mappings. When sufficient convergence and/or stabilization occurs or begins to occur, the center 606 may download the patient-specific calibration to the device 102.

The measurement process 700 also includes Step 706, where the device 102 enters a verification phase. During verification, invasive measurements, such as strip measurements are taken, to ensure that the calibration has converged. For example, in an embodiment, the data processing center 606 has downloaded a patient specific calibration to the device 102. Accordingly, the device generates optical absorption data, associated strip readings, and from its downloaded calibration, noninvasive glucose measurements. These now three associated pieces of data can advantageously be uploaded to the data processing center 606 and the newly found noninvasive glucose measurements can be verified as being accurate according to the expected and downloaded patient-specific calibration. Thus, advantageously, in Step 706, the protocol proves or verifies that the device 102 is generating acceptable and accurate noninvasive glucose measurements and otherwise functioning properly. In an embodiment, the data processing center 606 reduces the data storage requirements for the device 102 by storing the data associated with the calibration protocol remote from the device 102. In other embodiments, the process 700 may occur entirely within device 102, or with other access to remote data systems.

In an embodiment, during Step 706, verification, noninvasive measurements are not displayed as they may still be in need of further calibration for a particular user. In an embodiment, about one (1) to about two (2) invasive measurements should be performed per day for up to about five (5) days. In an embodiment, the user takes noninvasive measurements with each of the invasive measurements in order to associate instrument readings with invasive results.

The protocol 700 also includes Step 708, where the device 102 enters a sustaining or maintenance phase. During this phase, invasive measurements, such as strip measurements are taken, to ensure the calibration has not drifted from previous calculations. In an embodiment, during this step, noninvasive measurements are displayed as frequently as they are taken. In an embodiment, invasive measurements can be about one (1) week apart.

The measurement process 700 also includes Step 710, where the device 102 compares current noninvasive measurements to determine whether such measurements are outside expectations. For example, in an embodiment, the device 102 uploads measurement data to the processing center 606. As disclosed above, such information may advantageously include noninvasive glucose measurements and corresponding optical absorption data sets measured by the sensor 104. The data processing center 606 may advantageously use the glucose measurements alone, or with additional physiological information about the user, to retrieve more generalized or stored optical absorption data sets associated with that measurement. For example, when the device 102 measures 125 mg/dL glucose and uploads that to the center 606, the center 606 may advantageously retrieve stored optical absorption data sets associated with 125 mg/dL. These stored sets may be idealized, generalized, specific for the user, or combinations of the above. The stored data sets are then statistically compared to the uploaded data set from the device 102 associated with its measurement of, for example, 125 mg/dL glucose. The statistical comparison may be a Gaussian comparison or other statistical comparisons that provide an indication of how similar are the data sets, e.g., the stored data set and the uploaded data set, each associated with a similar or same glucose measurement, in this case, 125 mg/dL glucose. When the sets begin to be sufficiently dissimilar, the center 606 may inform the device 102 that the measurements are no longer within expectations and the device should be recalibrated. In an embodiment, recalibration can be a full recalibration or a partial recalibration or simply a restart of one of the other phases.

Figure 8:
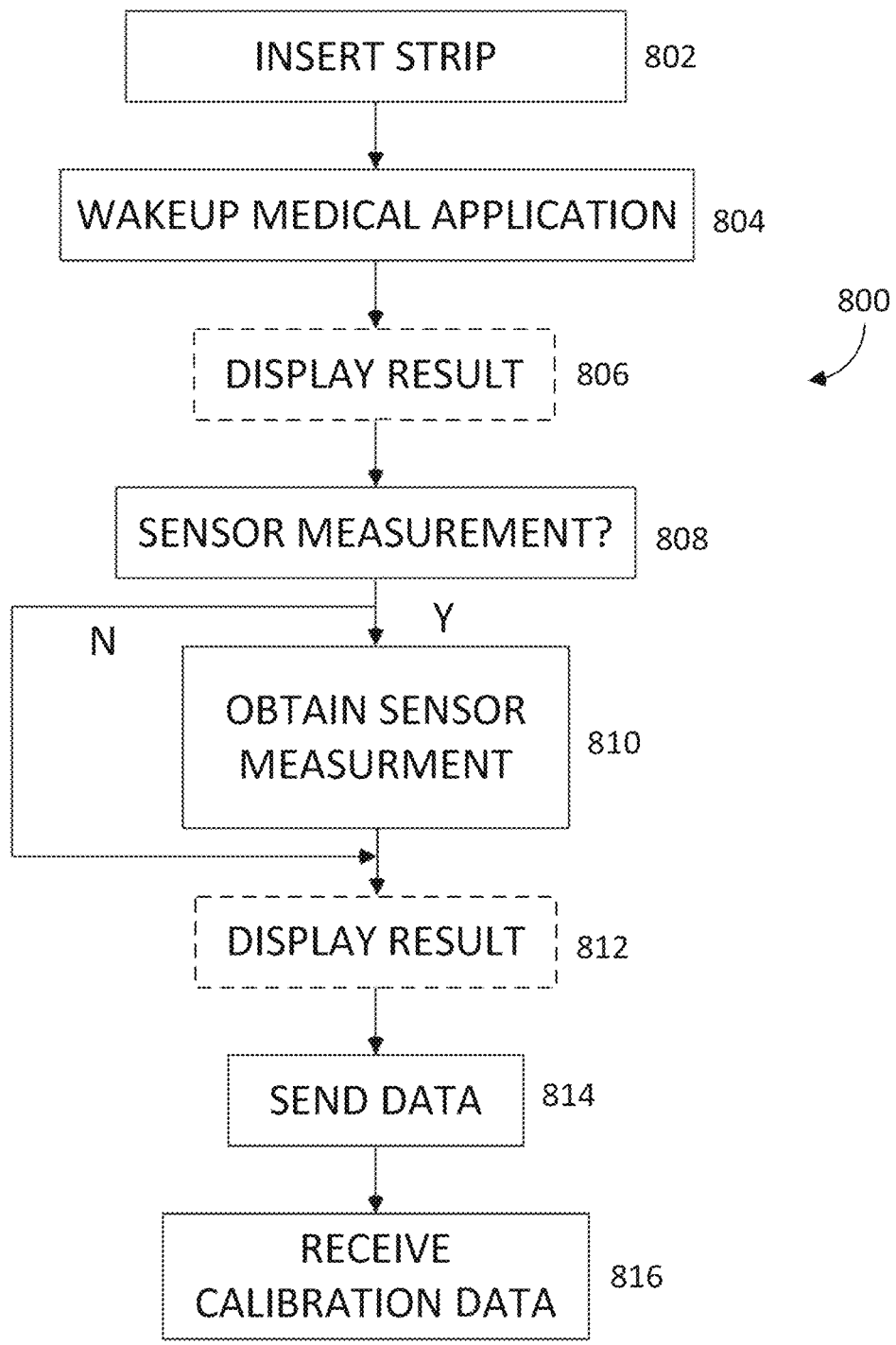
FIG. 8 illustrates a simplified minimally invasive strip measurement process according to an embodiment of the present disclosure.

FIG. 8 illustrates a simplified minimally invasive strip measurement process 800 according to an embodiment of the present disclosure. The process 800 includes Step 802, where a strip with the user's blood is inserted into the strip reader. In Step 804, a medical application wakes up and takes priority of any necessary shared resources in the processing device 102. The reader determines an output and forwards the output measurement to the medical application. In Step 806, the application may determine to optionally display the result, particularly when the result indicates an abnormal condition or a trend is moving toward an abnormal condition. In Step 808, the application determines whether a noninvasive measurement is desired, such as, for example, when the device 102 is performing a calibration or other phase, where, for example, timewise-commensurate minimally and noninvasive measurements are desired. In Step 810, the application may prompt the user to begin a noninvasive sensor measurement process, such as process 900, disclosed herein. In Step 812, the application may determine to optionally display the minimally invasive result, particularly if the result was not displayed above. In an embodiment, the application may display both results, only one result, a result in which there is an associated higher confidence, or a combination of the results. In Step 814, the measurement values are uploaded to one or more remote data processing centers. Other information may also be uploaded, such as, for example, spot check purchasing information, version information, demographic information, device information, use information for the device, the sensor, and/or the cable, or the like. In Step 816, the application may determine that the center is ready to download information to the device 102. For example, the center may have updated calibration information based on current or previous uploads, other users uploads, the calibration may be beginning or actually stabilizing and/or converging, or the like. Moreover, the center may download spot check purchasing information, other application information, or the like.

Figure 9:
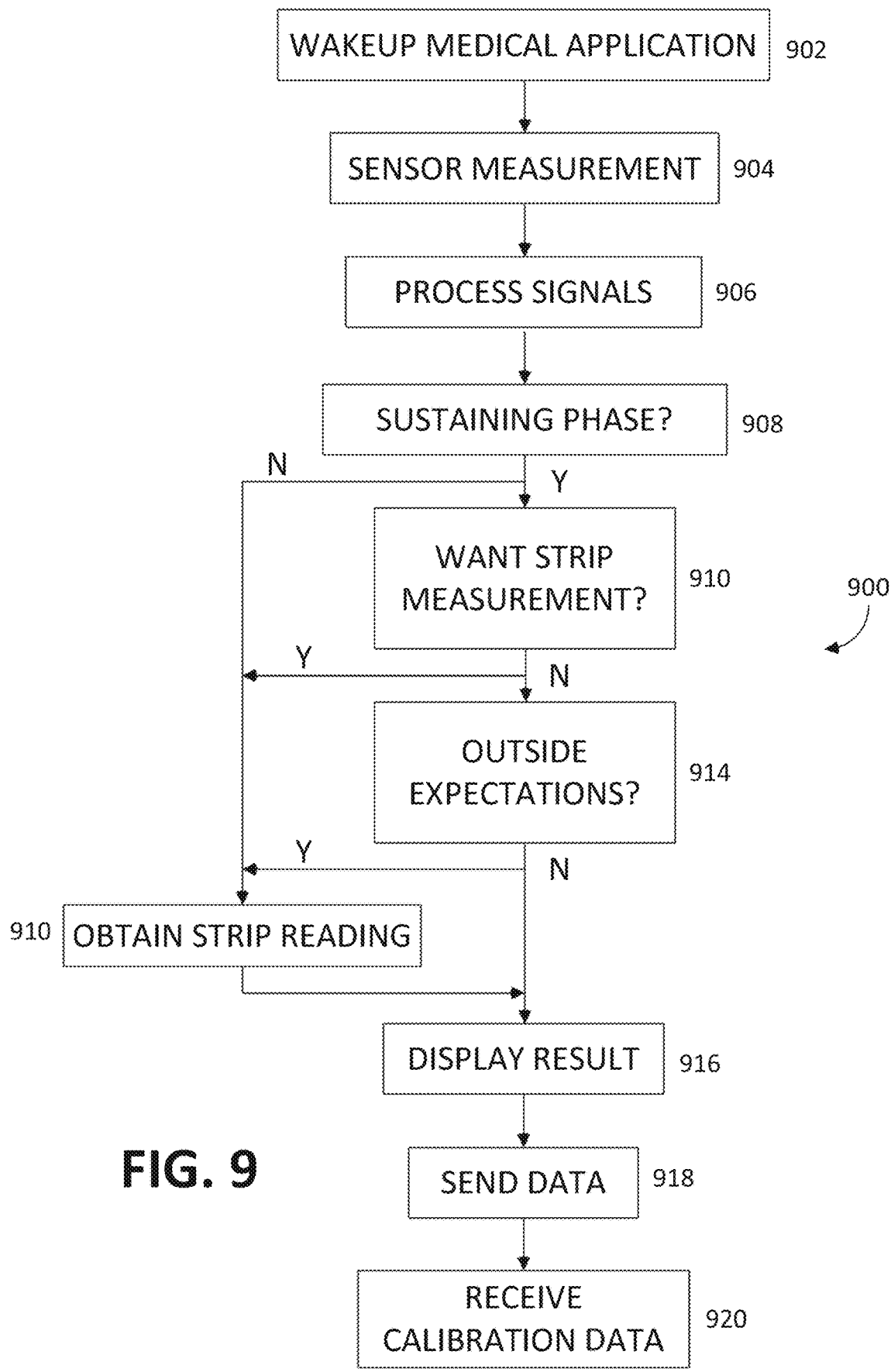
FIG. 9 illustrates a simplified noninvasive sensor measurement process according to an embodiment of the present disclosure.

FIG. 9 illustrates a simplified noninvasive sensor measurement process 900 according to an embodiment of the present disclosure. The process 900 includes Step 902, wherein if not already, the user wakes up the medical application. In Step 904, the user attaches the sensor 104 to a digit and activates a test input, such as a button on the touch screen of the device 102. In Step 906, the device 102 processes the detector signals to determine noninvasive glucose measurement values. In Step 908, the application determines whether the device 102 has been sufficiently calibrated with invasive measurements. If not, the application requests in Step 910 that an invasive measurement be taken. In Step 912, even when the device 102 is sufficiently calibrated, additional less frequent invasive measurements may be recommended to ensure accurate noninvasive performance. In Step 914, the application determines whether the processed noninvasive measurement is within expectations. In an embodiment, the device may include limits for its calibration, may include data sets for certain calibrations, may include confidence indicators for particular measurements based on, for example, the optical signal processing, or the like to understand whether current measurements are outside expectations. In Step 916, the application displays, when appropriate, the noninvasive measurements. In Step 918, the measurement values and/or other information are uploaded to one or more remote data processing centers. In Step 920, the application may receive information from the data center.

Figure 10:

FIGS. 10-19 illustrate exemplary user interfaces of the processing device of FIG. 1, according to various embodiments of the present disclosure. As shown in many of the user interfaces, familiar smart phone icons may be used such as, for example, battery power, time, connectivity such as Bluetooth or Wi-Fi, 3 G or higher connectivity, cellular connection signal strength such as increasing bars, and the like. Additionally, in the case of a spot check device, the device may include a readily identifiable indicator for the amount of measurements reaming or otherwise paid for. For example, FIG. 10 shows a "220" with a green check to indicate the user has prepaid or otherwise received 220 spot check measurement credits.

Moreover, FIG. 10 illustrates an exemplary test result interface, which may advantageously show the available scale, the severity at each end of the scale in alternating colors, such as, for example, green when the measurements are normal, yellow on each side as they move away from normal and red where measurements are abnormal.

Figure 11:
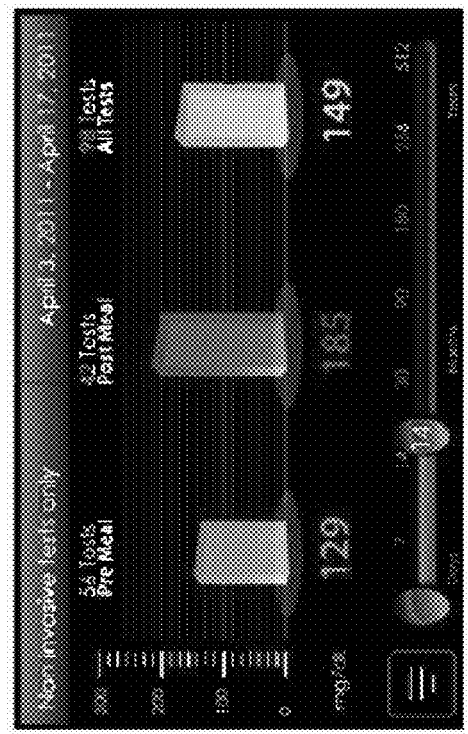

FIG. 11 illustrates an exemplary bar graph interface which may, for example, show readings during different activities for a particular time period. For example, FIG. 11 shows a collection of readings before and after meals, and numerically provides a combination of those readings. In an embodiment, the combination is a simple average. In other embodiment, the combination may be more statistically sophisticated and/or appropriately weight confidence indications associated with particular readings. In an embodiment, the scale at the bottom of the interface shows the time period of the combination, such as, for example, the simple average. In this case, the user has selected to average 14 days. As shown, the user could select days, months, or years, and then slide the bar for a numerical value of the same, and the processing device 102 would combine the stored measurement values over the corresponding time for display in similar fashion. Other activities around which one may wish to summarize measurement values may include exercise, snacks, specific dietary intake, times of day or week, or the like.

Figure 12B:
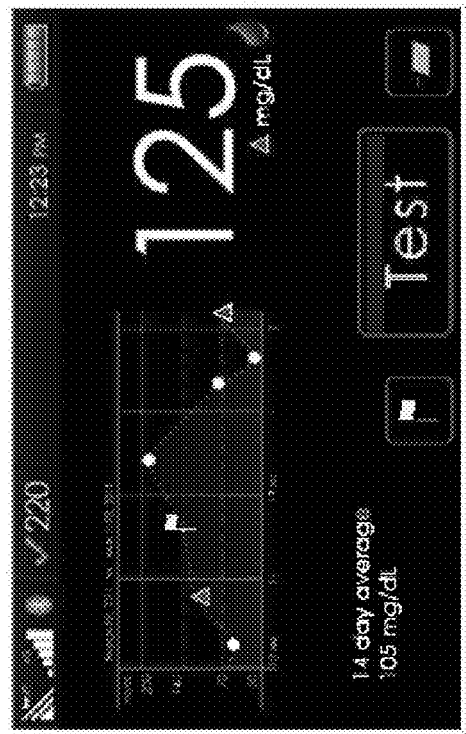
FIGS. 12A-12B illustrate exemplary result and trend interfaces.
Figure 12A:

FIGS. 12A-12B illustrate exemplary result and trend interfaces. For example, FIG. 12A may show basic information for noninvasive measurements, along with a trend showing readings over time. The trend may advantageously include flags for entered activities, may highlight abnormal or trending toward abnormal behaviors. In the particular embodiment shown, the round points indicate noninvasive measurements and the triangle points indicate strip or otherwise invasive measurements. Moreover, the trend may be selectable to review information available for the selected point in time. An activity log may also be shown. FIG. 12B may show similar basic information for invasive measurements, and switch the location and/or color to ensure a user can readily recognize the difference between the display of invasive and noninvasive values. Other icons or text may also be used to distinguish the measurements, such as, for example a blood droplet and/or triangle to indicate a strip measurement being displayed.

Figure 13B:
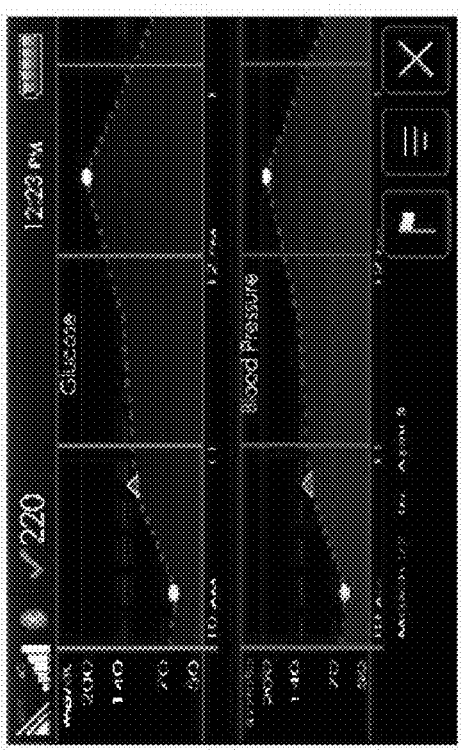
FIGS. 13A-13D illustrate exemplary trend interfaces.
Figure 13D:
Figure 13A:
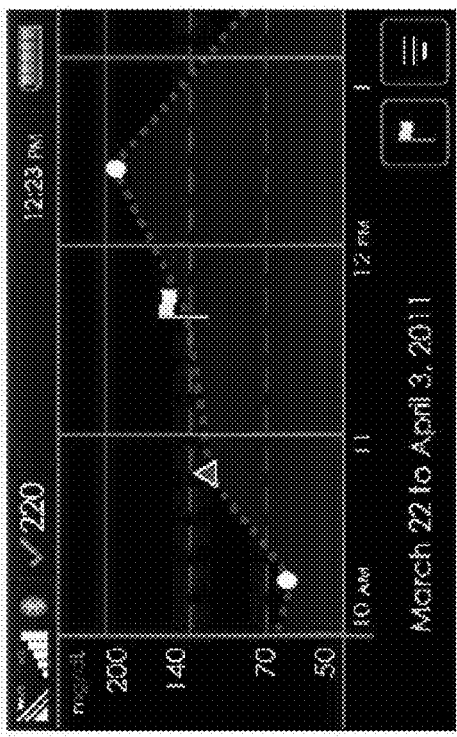
Figure 13C:
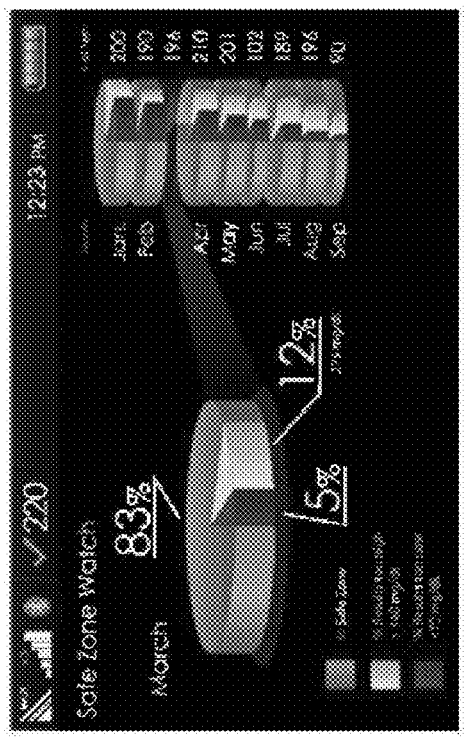

FIGS. 13A-13D illustrate exemplary trend interfaces. FIG. 13A illustrates an exemplary single trend of glucose measurements. In an embodiment, the trend may show both invasive and noninvasive measurements or may include trend lines for each type. Also, the trend line timeframe, or displayed time period, may be configurable through, for example, a pinch or dual finger parting to respectively shorten or lengthen the time period. FIG. 13B illustrates exemplary trends of multiple parameters, in this case, glucose and blood pressure, over the same time period so that, for example, a caregiver can readily recognize or identify how events in the multiple physiological parameters affect a particular parameter. For example, the user could readily review whether spikes or falls in blood pressure have any correlation to glucose readings. FIG. 13C illustrates how many normal, approaching abnormal, and abnormal measurements were taken over a period of time. FIG. 13D shows that additional information can be viewed when selecting a particular set of values, in this case, the set of abnormal measurements. As shown, the user selected a particular time period, and within that time period, the user selected the abnormal readings. Thus, the device 102 displays the measurement data, such as value, date, time, or the like, associated with each abnormal reading in the set.

Figure 14A:
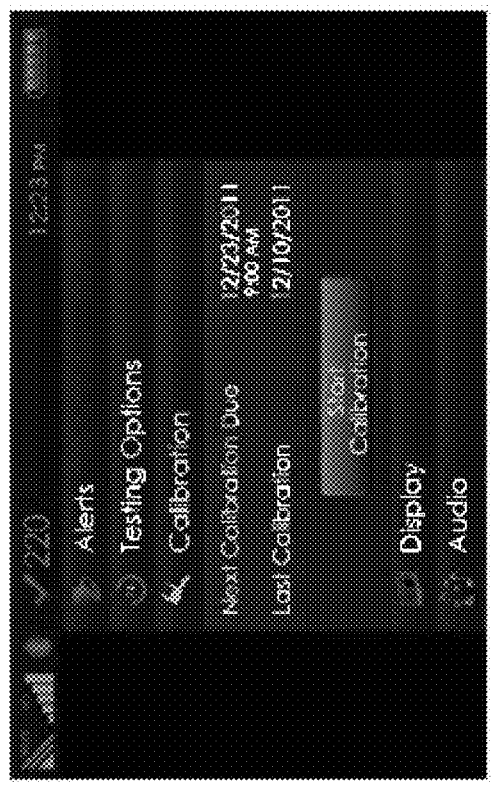
FIGS. 14A-14B illustrate exemplary calibration protocol interfaces.
Figure 14B:
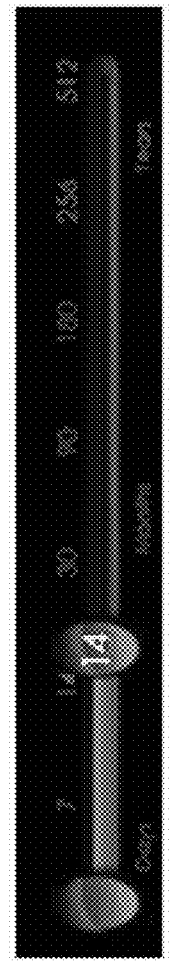

FIGS. 14A-14B illustrate exemplary calibration protocol interfaces. Particularly, FIG. 14A shows a user their progress through a calibration protocol, such as the protocol shown in FIG. 7. In an embodiment, the information displayed may include time and date of last calibrations and next calibrations, may include information on how many calibrations have been accomplished and/or how many remain. FIG. 14B illustrates how the applications can guide a user through a calibration process. For example, a timeline may advantageously indicate where in a calibration process the current measurements fall. Moreover, the timeline may include days, months, and years tabs to quickly organize information regarding device usage.

Figure 15A:
FIGS. 15A-15D illustrate exemplary alarm interfaces.
Figure 15B:
Figure 15C:
Figure 15D:

FIGS. 15A-15D illustrate exemplary alarm interfaces according to embodiments of the disclosure. In FIG. 15A, a measurement may indicate that a user's glucose levels are low and may indicate an alarm by any of placing an icon, such as a bell, on the display, enclosing the display in a red square, and/or highlighting on a trend graph the low measurement. In some embodiments, the bell is placed low when the glucose levels are abnormally low, or high, when they are abnormally high (FIG. 15B). Other more traditional visual and/or audio alarms may also be used including flashing display items or sounding audible alarms, the intensity or frequency of which might vary to show severity. In FIG. 15B, a measurement may indicate that a user's glucose levels are high. In FIG. 15C, abnormally high measurements may trigger a message to see a physician immediately, contact emergency services, check ketone levels or the like. Moreover, additional icons, such as ringing multiple bells, or other icons may be used to show significant severity. In FIG. 15D, a delta alarm may indicate the direction of change. For example, a low glucose level that is trend-wise dropping, indicates a more dangerous condition than one that is trend-wise raising. Icons and other information may be highlighted to indicate these conditions.

Figure 16A:
FIGS. 16A-16C illustrate exemplary instructive interfaces.
Figure 16B:
Figure 16C:
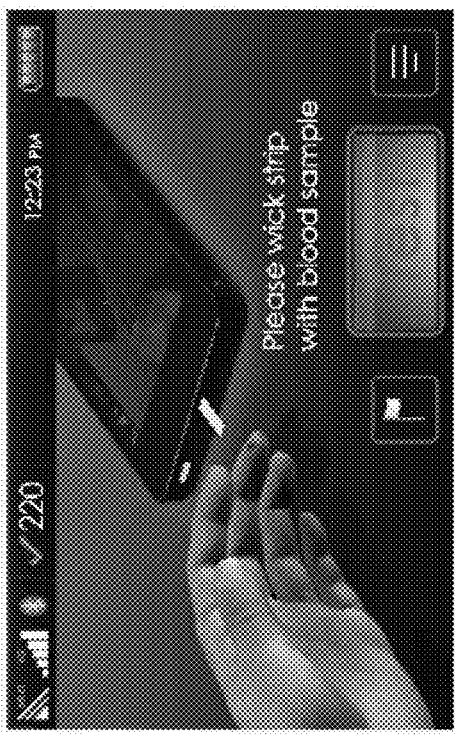

FIGS. 16A-16C illustrate exemplary instructive interfaces, such as test strip insertion guidance (FIG. 16A), general information about glucose measurements and glucose normality ranges (FIG. 16B), or pricing information for instrument usage (FIG. 16C). In FIG. 16A, the instructive interface may also guide the user in calibrating or verifying strip reader measurements. For example, often strip reader manufacturers provide solutions for testing strip readers. The user drips solution onto a test strip and inserts the strip into the reader. The solution is designed to cause the reader, when functioning properly, to provide a measurement within a provided range of acceptable measurements. These solutions will often include three bottles corresponding to low, regular or medium and high solutions, designed to cause the reader to provide measurement in the low, medium and high ranges. The interface may guide the user through, for example, using these solutions to verify accurate operation of the strip reader.

In FIG. 16C, the user may interact with the device to purchase additional spot checking credits. Spot checking accounting is disclosed in U.S. Pat. App. Pub. No. 2011-0172498, filed Jul. 14, 2011 titled "Spot Check Monitor Credit System," incorporated by reference herein.

Figure 17:
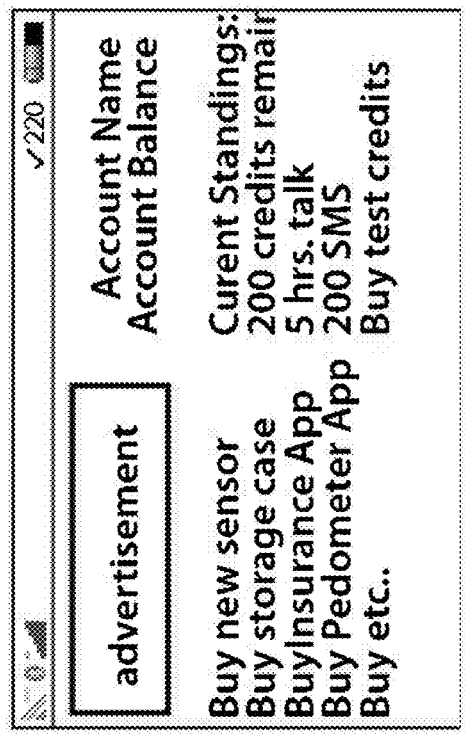

FIG. 17 illustrates an exemplary application interface showing, for example, different types of medical and non-medical applications that might be executed by the processing device 102. For example, the applications may include noninvasive and minimally invasive glucose testing, internet browsing, email, texting, video conferencing, cellular phone, graphs, activities or calendaring, flag or activity management, weather, photographs or videos, camera or video operation, calibration protocols, electronic interference detection, such as that disclosed in U.S. is disclosed in U.S. Pat. App. Pub. No. 2011-0109459, filed May 12, 2011 titled "Interference Detector for Patient Monitor," incorporated by reference herein, music, spot check purchasing applications, such as those disclosed above, general questions and setting preferences, facebook, twitter, map or navigation, address book, internet bookmarks, downloadable applications of all sorts, and the like.

Figure 18A:
FIGS. 18A-18B illustrate exemplary events interfaces including a food flag interface.
Figure 18B:

FIGS. 18A-18B illustrate an exemplary events interfaces including a food flag interface. One application that may be extraordinarily helpful for, for example, a diabetic trying to manage their glucose levels is to include easily entered activities into a calendar program. These activities or flags are associated with events such as fasting, insulin, food/drink intake, measurement, exercise, and the like. FIG. 18B shows an exemplary interface presented when the user wants to enter an eating activity. As shown, the information may include the amount of carbohydrates in the food, the portion or size, the glycemic index or the like. As is understood by an artisan, the glycemic index includes ranges of about fifty five (55) or less for most fruits and vegetables, legumes/pulses, whole grains, nuts, fructose and products low in carbohydrates, about fifty six (56) to about sixty nine (69) for whole wheat products, basmati rice, sweet potato, sucrose, baked potatoes, and about seventy (70) or above for white bread, most white rices, corn flakes, extruded breakfast cereals, glucose, maltose.

Figure 19A:
FIGS. 19A-19B illustrate exemplary priority interfaces.
Figure 19B:
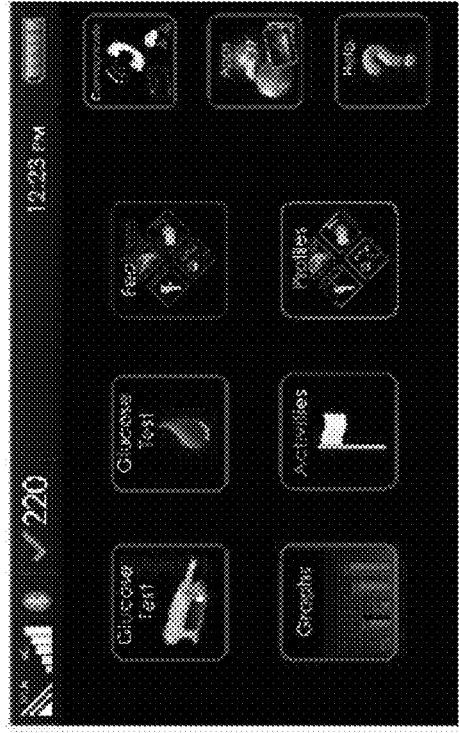
Figure 22A:
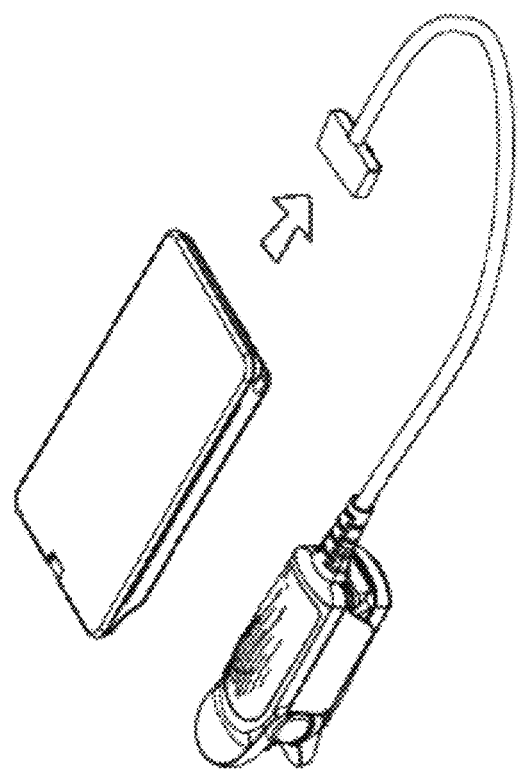
FIGS. 22A-22D illustrate priority mode glucometers according to embodiments of the present disclosure showing connected and disconnected sensors and inserted and removed test strips, respectively.
Figure 22B:
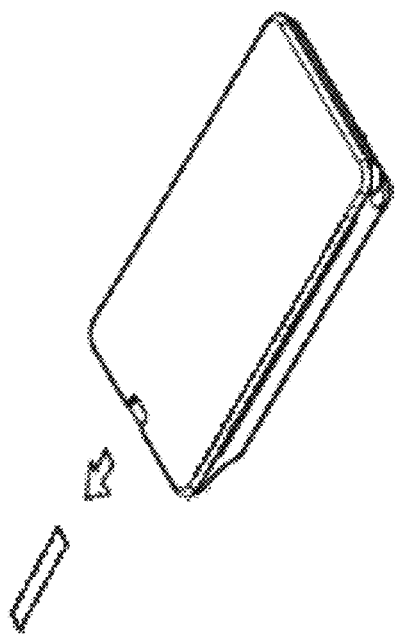
Figure 22C:
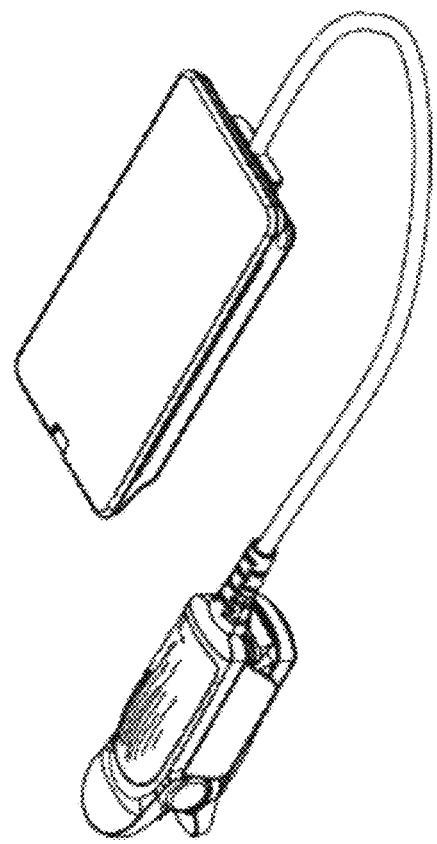
Figure 22D:
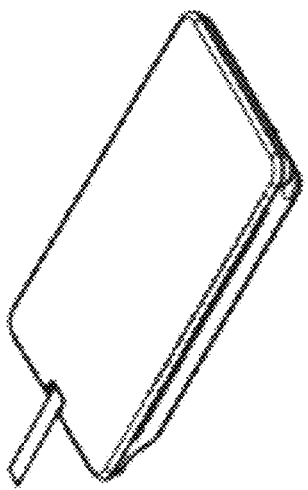

FIGS. 19A-19B illustrate exemplary priority interfaces. As will be disclosed in more detail below, certain applications will be designed to take a priority over other applications. In general, medical applications, such as those of FIG. 19A, will take priority over others, such as those of FIG. 19B. Moreover, in an embodiment, the order the icons appear within a figure may visually provide the user with an understanding of their priority. For example, in FIG. 19B, incoming phone activity takes priority over incoming email activity, etc. In an embodiment, the manufacturer sets the medical priorities over the nonmedical priorities. In an embodiment, the user may be able to add applications to one or both priority interfaces to reorder default priorities; however, the default priorities for certain applications may not be editable to ensure safe operation of the device.

FIG. 20 illustrates a priority mode processing device having medical related functions and non-medical related functions sharing common resources. Advantageously, the processing device has a priority mechanism so as to prevent the medical related functions from competing with the non-medical related functions for the common resources during critical time periods. These critical time periods are indicated by triggering events. In particular, a triggering event indicates to the system that the medical related functions have resource priority. This priority may be, for example, exclusive access to and use of displays, alarms, controls, communications and processing power so as to make time critical patient health and risk assessments and output those assessments in a timely manner to a healthcare provider.

FIG. 21 illustrates a priority mode processing device embodiment having a smart phone or other cellular communication device sharing one or more common resources with a processing device. The common resources may include operating system functions, processor cycles and input/output access, to name a few. A priority mode for the processing device may be triggered by the connection or disconnection of a device to the monitor, such as a sensor or sample, advantageously giving the monitor maximum access to processing and input/output resources so as to respond to physiological data inputs and calculate medical parameters or conditions accordingly.

FIGS. 22A-22D are illustrations of priority mode glucometer embodiment. The glucometer is advantageously integrated in a handheld device having both processing device and smart phone capabilities. When a sensor or test strip is plugged or inserted into the handheld device, it is usable as a glucometer. When the sensor or test strip is unplugged or removed from the handheld device, it is usable as a mobile phone, such as, for example, a smart phone with many of today's smart phone applications and functions.

FIGS. 23-29, described in detail below, illustrate various embodiments that combine processing device and smart phone features in an advantageous manner so that the physiological measurements are not interrupted or delayed by smart phone functions, such as incoming calls and text messages to name a few.

Figure 23:
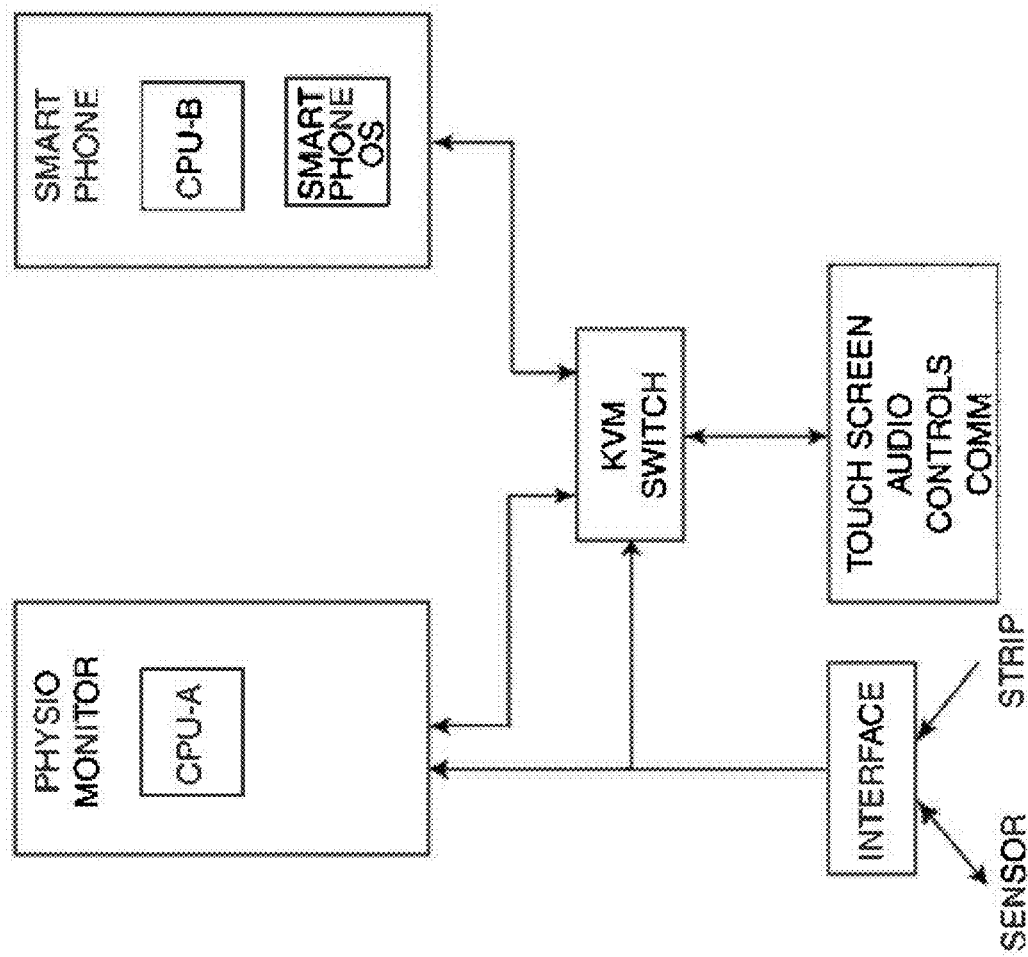
FIG. 23 illustrates a simplified block diagram of priority mode processing device utilizing a KVM switch for priority control according to an embodiment of the present disclosure.

FIG. 23 illustrates processing device embodiment that utilizes a KVM (keyboard/video/mouse) switch for priority control. The KVM switch controls access to the display, touchscreen and audio between a processing device CPU that runs the medical system and a smart phone CPU that runs the cell phone system.

Figure 24:
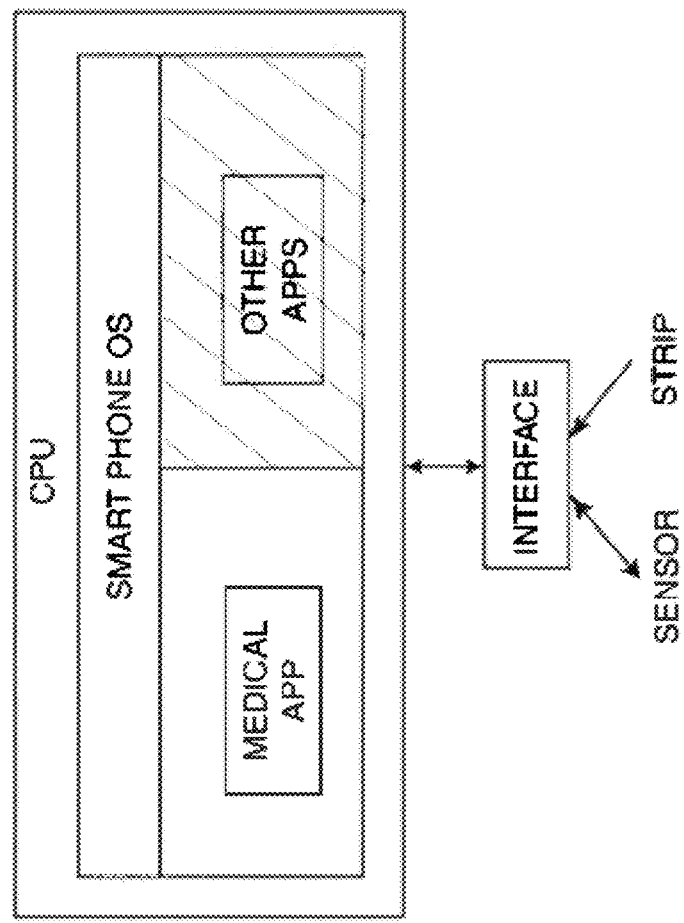
FIG. 24 illustrates a simplified block diagram of priority mode processing device utilizing an activated medical app for priority control according to an embodiment of the present disclosure.

FIG. 24 illustrates a processing device embodiment where the medical functions are implemented as a single application running on the smart phone operating system (OS), such as those offered by Google (Android), Windows, Apple, or the like. In an embodiment, when a sensor or strip is plugged into the device, the OS activates the medical application and all other applications are suspended and cannot be resumed until the sensor/strip is unplugged or some other user supplied input is provided.

Figure 25:
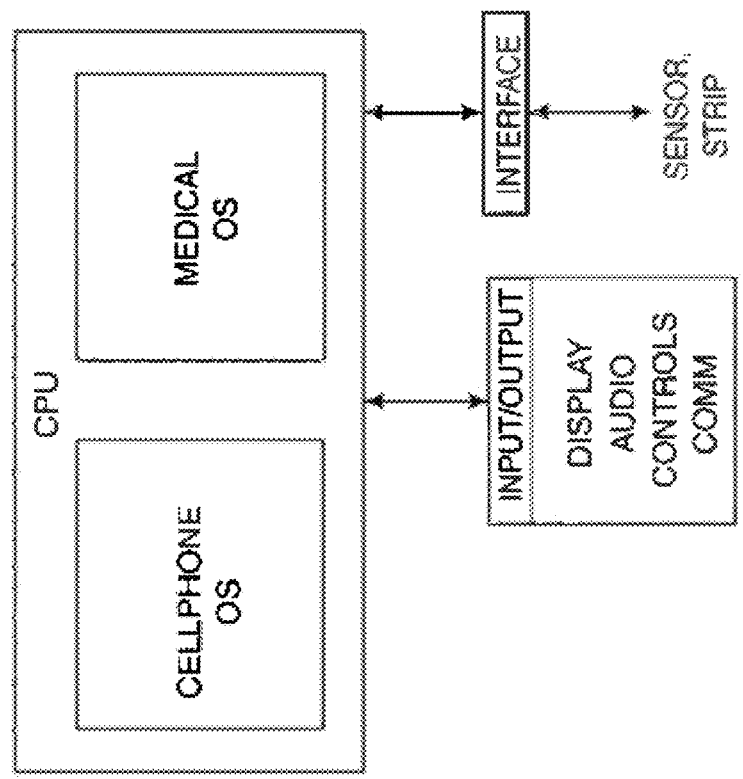
FIG. 25 illustrates a simplified block diagram of priority mode processing device utilizing separate virtual machines for priority control according to an embodiment of the present disclosure.

FIG. 25 illustrates a processing device embodiment where two separate operating systems run as virtual machines on the device CPU. The cell phone OS handles cell phone functions and the medical OS handles the medical system functions.

Figures 26, 27:
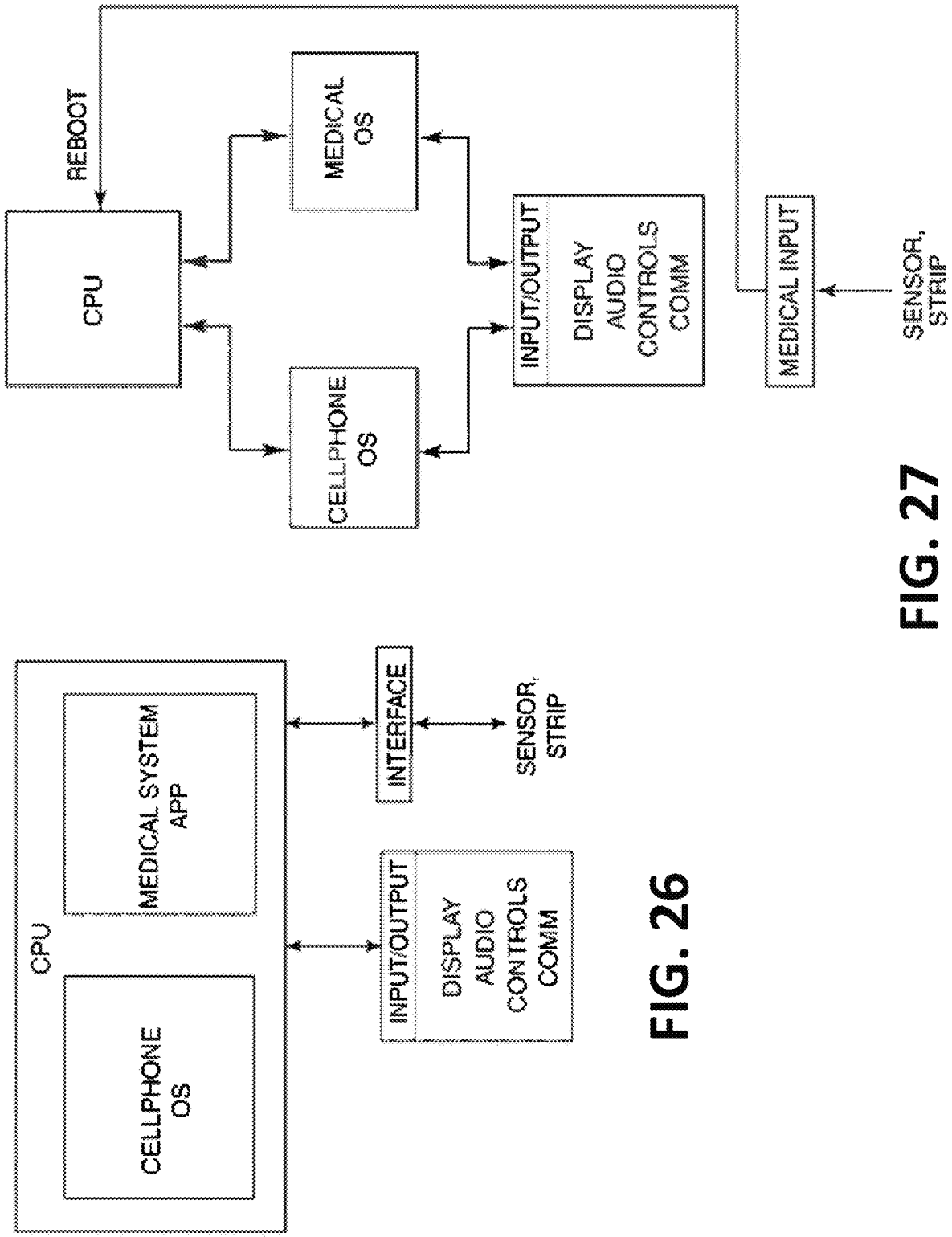
FIG. 26 illustrates a simplified block diagram of priority mode processing device utilizing a cell phone operating system that is suspended in favor of a medical system application when a sensor or strip is detected according to an embodiment of the present disclosure.
FIG. 27 illustrates a simplified block diagram of priority mode processing device having dual-booted operating systems according to an embodiment of the present disclosure.

FIG. 26 illustrates a processing device embodiment where the medical application runs next to the cell phone OS (e.g. Android). As soon as the sensor or strip is plugged into the device, the medical application is started and runs separate from the cell phone OS. The cell phone OS is suspended and the medical application takes control of the hardware, including the touch screen.

FIG. 27 illustrates a dual-boot processing device embodiment. As soon as a sensor or strip is plugged into the device, the cell-phone operating system is shut down and the device is rebooted into the medical operating system.

Figure 28:
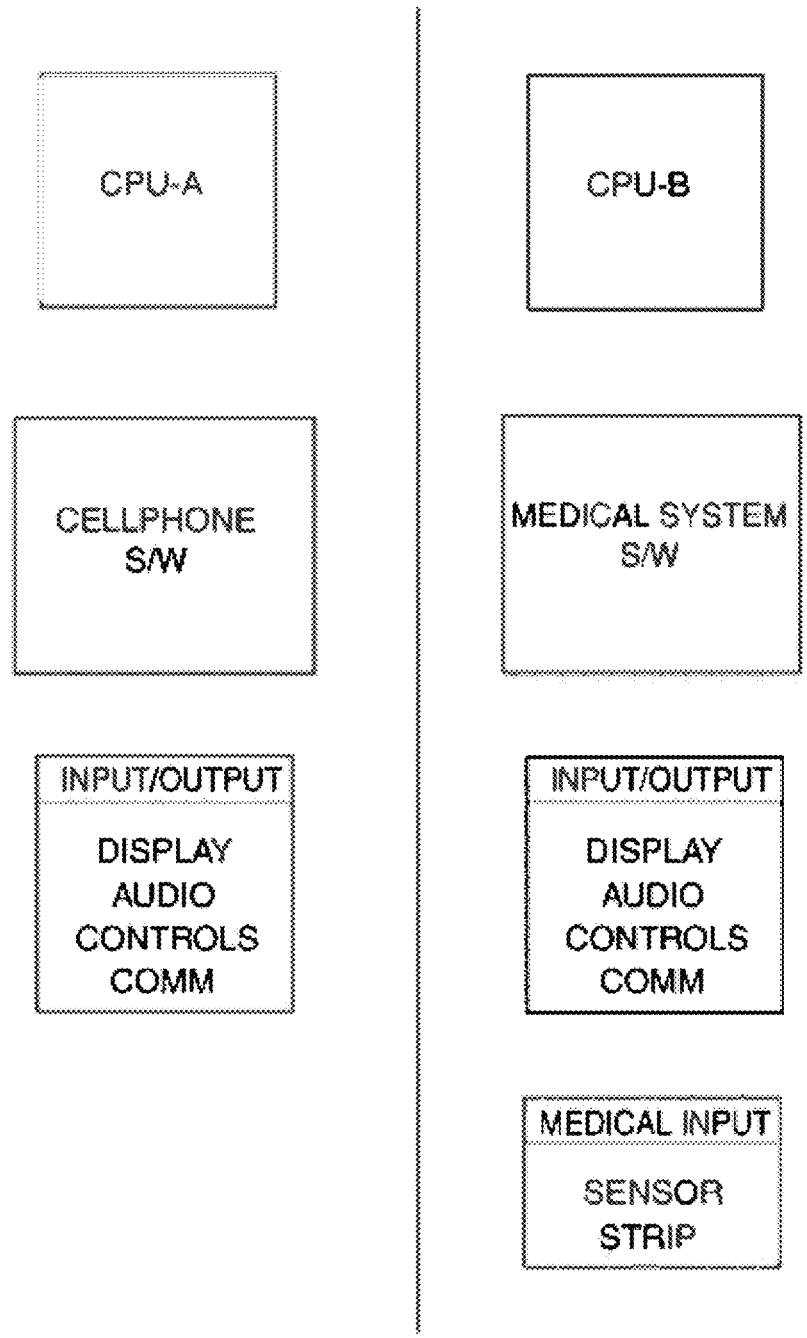
FIG. 28 illustrates a simplified block diagram of priority mode processing device having double-sided device functionality according to an embodiment of the present disclosure.

FIG. 28 illustrates a double-sided processing device embodiment. A first display is mounted on one side of the device with cell-phone functionality and a second display is mounted on the other side of the device with medical functionality. A related embodiment implements two separate systems (cell-phone and medical) in one (hardware) chip, such as a FPGA or ASIC.

Figure 29:
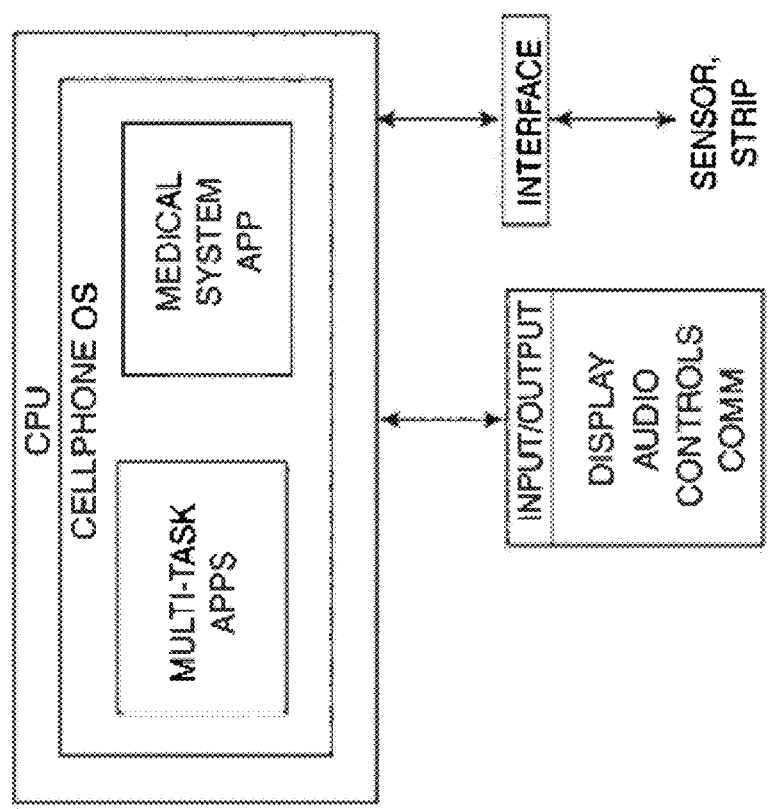
FIG. 29 illustrates a simplified block diagram of priority mode processing device running a single medical application in lieu of a multi-task normal operating mode according to an embodiment of the present disclosure.

FIG. 29 illustrates a processing device embodiment where the cell phone as (e.g. Android) runs a single medical system application while a sensor and/or strip is plugged into the device. When the sensor or strip is removed, the OS runs in a normal al operating mode, multitasking various applications.

A priority mode processing device has been disclosed in detail in connection with various embodiments. These embodiments are disclosed by way of examples only and are not to limit the scope of this disclosure. One of ordinary skill in art will appreciate many variations and modifications.

In an embodiment, the features and functionality of the processing device 102 may be incorporated into smart phone technologies. For example, a smart phone may enables patients and healthcare personnel to manage health data, and in particular, physiological reading data from one or more health data collection devices such as a glucose sensor or pulse oximeter.

Figure 30:
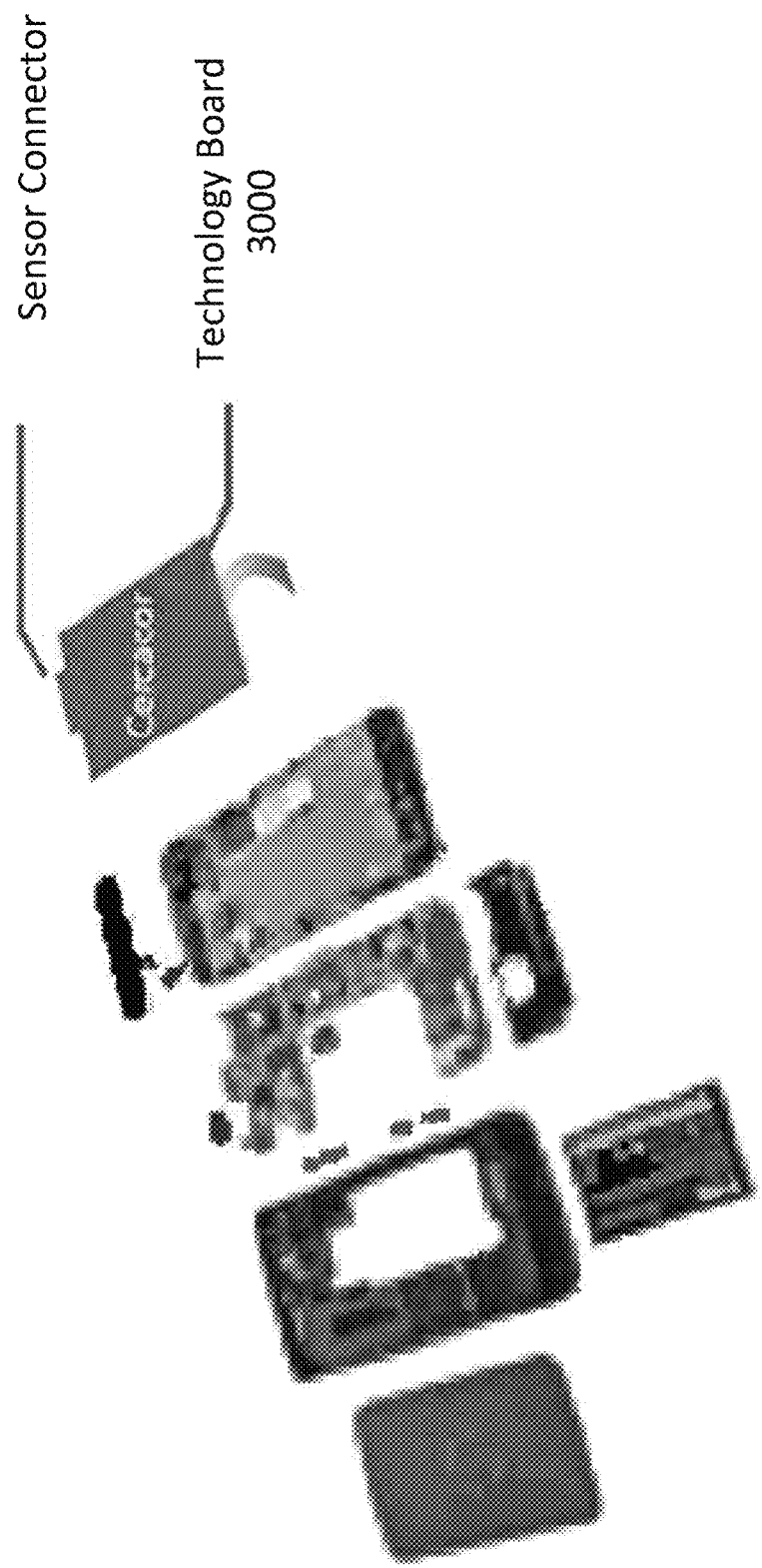
FIG. 30 illustrates a simplified exploded view of an expanded smart phone including internally integrated medical processing capability according to an embodiment of the disclosure.
Figure 32:
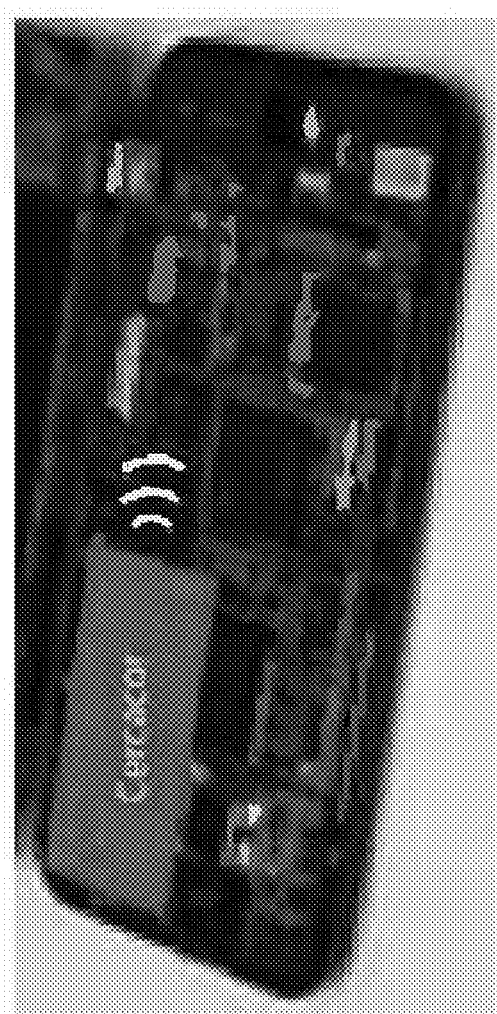
FIGS. 32-34 illustrate medical processing cartridges as separate units communicating to create an expanded smart phone according to embodiments of the disclosure.

FIG. 30 illustrates an exploded view of a smart phone including internally integrated processing capability, such as, for example, a processing board or other device. As shown, the technology board 3000 comprises an integrated board within the smart phone housing. The board communicates with an external optical sensor, such as sensor 104. In various embodiments, the sensor provides an output signal indicative of an amount of attenuation of predetermined wavelengths (ranges of wavelengths) of light by body tissues, such as, for example, a digit, portions of the nose or ear, a foot, or the like. The predetermined wavelengths often correspond to specific physiological data desired, including for example, blood oxygen information such as SpO2, blood glucose, total hemoglobin, methemoglobin, carboxyhemoglobin, bulk tissue property measurements, water content, pH, blood pressure, respiration related information, cardiac information, indications of perfusion, or the like. The smart phone may also include software such as an application configured to manage output measurement data from the processing board. The application functionality can include trend analysis, current measurement information, alarms associated with below threshold readings or reminders to take measurement data at certain times or cycles, display customization, iconic data such as hearts beating, color coordination, bar graphs, gas bars, charts, graphs, or the like, all usable by a caregiver or smart phone user to enable helpful and directed medical monitoring of specified physiological parameters.

The smart phone may advantageously be capable of connecting to and receiving data from a physiological data collection device such as an optical sensor glucose sensor. The smart phone is able to connect to a data collection device and receive data from the device. The smart phone may be configured to analyze data from the device, display data from the device, and otherwise utilize the data to empower the user to take control of his health.

The smart phone may have a fully integrated technology board which receives and analyzes data from the collection device. The technology board may alternatively be housed within a removable cartridge. The board may employ RF shielding. The smart phone may utilize a Samsung GHz processor or the like. The processor may utilize mDDR2 or mDDR, or the like. In some embodiments, the processor may employ MLC NAND 48 TSSOP flash memory technology or the like. The smart phone may comprise a power management integrated circuit with on/off/wakeup capability.

In an embodiment, the smart phone may utilize one of a number of different operating systems. For example, an android, linux, or qnx system may be used.

Software may be installed upon the smart phone that can analyze the data received from the sensor device and make it available in a way for the user to manage his health. There may be software which allows a user to view the data in a multitude of ways. The smart phone may also be able to alert the user to an abnormal data reading. The software may also alert the user to take a physiological reading or medication. It may have the capability of sending physiological data to a home computer where the user manages his health data. The data can also be sent to a physician or pharmacist for their expertise and feedback.

The smart phone through the board may include an input that can connect to the data collection device or optical sensor. In some embodiments this sensor may be on the top portion of the smart phone, integrated into the smart phone housing or housing attachment, or a separated device as shown. The connector may be chosen from a variety of connectors including a snap click connector, a magnetic connector and/or a multi pin connector. In some embodiments, the smart phone may comprise a magnetic latch sensor port with dual orientation with allows for a controlled break away. In an embodiment, the sensor includes active pulse technology designed to provide a perturbation of the tissue during measurements.

The smart phone may have a display that is between about 3" and about 5" or more. A bigger screen may advantageously allow more versatility from a user experience perspective. The display may have the capability of switching between a portrait and a landscape mode based on user preference or automatically based on positioning. The display, in some embodiments, has a wide viewing angle in both portrait and landscape mode. It may have a backlight in one of both of the modes. In some embodiments, the resolution is around about 960×640 with a 24 bit rate.

The display may be a projective capacitive LCD screen. The screen may be made from impact resistant materials such as gorilla Glass®, sapphire crystal or polycarbonate. The conductive coating may be made of a variety of materials including indium tin oxide (ITO). The screen may be a multi input screen with 3 or more inputs. The screen may also support gestures such as an x/y swipe inertia scroll, presshold, 2 point pinch zoom, 3 point pinch zoom and swiping. In some embodiments, the smart phone is capable of utilizing haptic technology to communicate with the user. This feature may be useful to alert a user to significant changes in physiological measurements. The device may also utilize a bezel to maneuver around the display.

The smart phone may comprise a power button. The button may be a tactile button that produces an audible click. The button may be located on a side of the smart phone.

The smart phone may include a chargeable battery to provide power to the device. In some embodiments, the battery may be a 1500-3000 mAh lithium battery. The battery may be housed in a recess of the smart phone covered by a removeable battery door. This may be located on the back of the phone.

The smart phone may additionally comprise an AC power input. In some embodiments, the input is located on a side of the device. Alternatively, the device may be inductively charged.

The smart phone may also comprise one or more USB ports. The ports may be regular or micro USB ports. The ports may utilize a USB switch such as a Fairchild switch. The USB port may be capable of charger detection, audio and UART detection. The USB ports may be located on a side of the smart phone.

The smart phone may be capable of wireless communication. This may be achieved through a wireless connection such as a Broadcom 802.11 a/b/g/n dual band connection. It may also utilize a Bluetooth connection, an FM receiver using an RDS standard, or the like. The smart phone may also comprise a module to allow for connectivity to networks such as the 3G network, 4G network, and the like.

The smart phone may contain a speaker and/or an earphone jack located on it. In some embodiments, the speaker is a multi-directional speaker for audio over air. The speaker may be capable of 85 db. The smart phone may further comprise an amplifier. The amplifier may be a 3 W filter-free class D mono audio amplifier in some embodiments. A volume control may be located on the phone. In some embodiments, the volume control may be a volume rocker switch.

The smart phone may comprise a camera. The camera may be a video and/or still camera. The smart phone may contain a camera on the front side and rear side of the phone to enable things like self-portraits and video chats. In some embodiments, the front camera is a 1.3 MP camera. In some embodiments, the back camera is an 8 MP camera. The camera(s) may also comprise a flash which may be an LED flash.

Some or all of the part of the device not making up the screen may be comprised of a variety of materials including liquid metal, CNC aluminum, and Hydro Formed aluminum. Soft touch paint may be applied.

The smart phone may comprise high durometer bumper fins to protect it from drops and everyday wear and tear. The fins may comprise a material that is not temperature sensitive, has a generally high chemical resistance, is flexible, and is durable. In some embodiments, this material may be multi-shot santoprene or another thermopolastic elastomer. The fins may be located on the rear side of the smart phone, at the top and bottom of the device. There may be between 1 and 5 fins located on both the right and left sides of the smart phone. The fins may extend towards the top of the device and wrap around to cover a portion of the top of the device. The bottom fins may be designed in a similar manner.

The foregoing features are not intended to be exhaustive. The smart phone may contain additional features such as an acoustic speaker slot, a slot for Micro SD, HDMI outputs, a microphone, a sim card draw, an accelerometer and the like.

FIG. 31 illustrates insertable cartridges that may connect to, for example, a technology board or other interface on a general purpose smart phone. As shown in FIG. 31, the insertable cartridge may be function specific. It could be a glucose sensor cable cartridge. A glucose sensor may be integrated into the cartridge. The cartridge could alternatively be a temperature and blood pressure cartridge. The cartridge may be an environmental sensor, for instance, measuring CO in parts/million. It may be an extra battery cartridge. The cartridge may be a barcode scanner or other digital device interface for data import, software, application firmware upgrades or patient management. The cartridge could also provide general oximetry or cooximetry functionality and sensor connectivity, or may be acoustic sensor compliant and determine respiration parameters.

The smart phone device described may advantageously allow a user to carry only one unit rather than both a phone and a sensor device. As a result of its dual functionality, the device may be bigger and more costly than a traditional smart phone. Additionally a user may have to replace their existing phone. Another advantage is that the smart phone to be used as an 'on the go' health organizers. This setup also allows the user more technology options. For example, glucose readings as well as pulse oximetry readings may be received by the smart phone device. It is also easier to input information using the smart phone device, particularly when the user has to re-calibrate the device on a weekly basis.

Figure 33:
Figure 34:
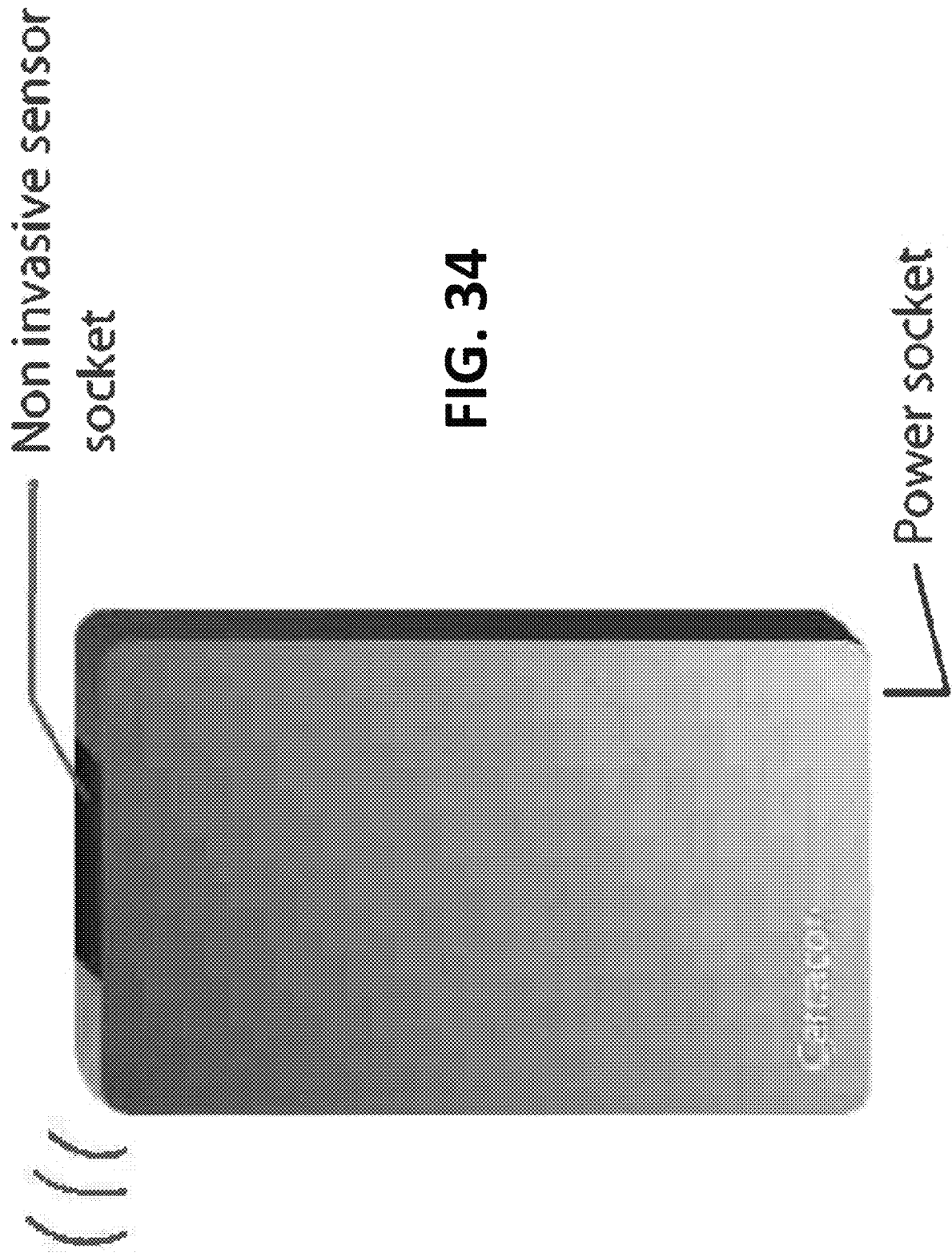

In another embodiment of the smart phone device, the technology board with the integrated data collection device may be a separate unit from the smart phone. In FIGS. 31-34, the smart phone may include a wireless chipset (FIG. 32) that communicates with stand-alone data collection devices (FIG. 33-34). The stand-alone devices may provide functionality similar to any individual or combination of the cartridges mentioned in the foregoing. The wireless chipset my provide UWB, Bluetooth, Zigbee, and wireless USB connectivity.

The stand-alone units provide for smaller more portable smart phones, Additionally, the user has the option to carry the smart phone and sensor device together or separately, which could be less cumbersome. In some embodiments, the units may include a display. The unit may communicate with a smart phone to better present measurement information, processed information, and/or trend information to a user on more advanced smart phone displays. The unit may be capable of wireless communication with any mobile phone or computer. The unit will need to be able to connect to an external computing device in order to calibrate.

One significant advantage of the smart phone embodiments is that the smart phone manufacturers, and not the medical device manufacturer, has invested the resources into developing and commercializing the processing used for nonmedical applications. Development of this hardware and software is thus lifted from a medical device focused company.

Although the foregoing processing device and smart phones have been described in terms of certain preferred embodiments, other embodiments will be apparent to those of ordinary skill in the art from the disclosure herein. For example, alternate protocols may be implemented or the like. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

All publications, patents, and patent applications mentioned in this specification are herein incorporated by reference to the same extent as if each individual publication, patent, or patent application was specifically and individually indicated to be incorporated by reference.

Moreover, terms used herein are intended to have their broad ordinary meaning understood within the art. The term "and/or" in intended to mean that one, any combination of two or more, or all combinations of the corresponding listed elements are appropriate; however, it is not intended to mean that all combinations must be accomplished.

What is claimed is:

1. A method of offloading from a local processing device to a remote processing device at least some of the data processing and storage functionality related to determining a wearer-specific calibration data, said local processing device including at least one local processor and operably communicating with at least one noninvasive physiological sensor, said local processing device local to a wearer of said noninvasive sensor, said remote processing device including at least one remote processor and operably communicating with said local processing device and a memory geographically remote from said wearer of said noninvasive sensor, said remote processing device also geographically remote from said wearer of said noninvasive sensor, said wearer-specific calibration data including at least portions of a mapping of noninvasive measurements to at least some clinically-determined measurements of physiological parameters of said wearer of said noninvasive physiological sensor, the method comprising:
  storing in said remote memory previously acquired measurements of said physiological parameters, at least some of said previously acquired measurements comprising generalized measurements not specifically associated with said wearer;
  generating sensor signals with said noninvasive physiological sensor, said sensor signals responsive to physiological parameters of the wearer of said noninvasive physiological sensor;
  determining with said at least one local processor measurements responsive to said sensor signals using a first calibration data;
  communicating said measurements to said remote processing device;
  comparing with said at least one remote processor said measurements with said previously acquired measurements;
  determining using said at least one remote processor said wearer-specific calibration data when said comparing calibrates said measurements to said previously acquired measurements;
  communicating said wearer-specific calibration data to said local processing device;
  generating additional sensor signals with said noninvasive physiological sensor, said additional sensor signals responsive to said physiological parameters;
  processing with said at least one local processor said additional sensor signals according to said wearer-specific calibration data to determine one or more wearer-specific calibrated measurements of said physiological parameter; and
  displaying display indicia responsive to said wearer-specific calibrated measurements.

2. The method of claim 1, wherein said communicating said measurements to said remote processing device and said communicating said wearer-specific calibration data to said local processing device comprise cloud communication.

3. The method of claim 1, wherein said generating sensor signals with said noninvasive physiological sensor comprises generating said sensor signals using an ECG sensor.

4. The method of claim 1, wherein said generating sensor signals with said noninvasive physiological sensor comprises generating said sensor signals using a blood oxygen saturation sensor.

5. The method of claim 1, wherein said generating sensor signals with said noninvasive physiological sensor comprises generating said sensor signals using one of a respiration sensor and an acoustic sensor.

6. The method of claim 1, wherein said generating sensor signals with said noninvasive physiological sensor comprises generating said sensor signals using a blood pressure sensor.

7. The method of claim 1, wherein said generating sensor signals with said noninvasive physiological sensor comprises generating said sensor signals using a temperature sensor.

8. The method of claim 1, wherein said generating sensor signals with said noninvasive physiological sensor comprises generating said sensor signals using a drug testing sensor.

9. The method of claim 1, wherein said generating sensor signals with said noninvasive physiological sensor comprises generating said sensor signals using a depth of sedation sensor.

10. The method of claim 1, wherein said determining using said at least one remote processor said wearer-specific calibration data when said comparing calibrates said measurements to said previously acquired measurements comprises determining using said at least one remote processor said wearer-specific calibration data when said measurements stabilize.

11. The method of claim 1, wherein said determining using said at least one remote processor said wearer-specific calibration data when said comparing calibrates said measurements to said previously acquired measurements comprises determining using said at least one remote processor said wearer-specific calibration data when said measurements converge toward said previously acquired measurements.

12. The method of claim 1, wherein said determining using said at least one remote processor said wearer-specific calibration data includes processing with said at least one remote processor addition physiological information about said wearer.

13. A monitoring system configured to provide a wearer of a noninvasive sensor measurements of physiological parameters of the wearer, the monitor comprising:
  said noninvasive sensor configured to output sensor signals responsive to a pulse rate of the wearer based on detection of attenuated light by said noninvasive sensor;
  a local processing device including a display and at least one local processor, said local processing device operably communicating with said noninvasive sensor to receive said output sensor signals, said local processing device geographically local to said wearer and said at least one local processor configured to determine said measurement of said pulse rate;
  one or more remote processing devices operably communicating with said local processing device and a remote memory, said one or more remote processing devices including at least one remote processor, said remote memory geographically remote from said wearer and said one or more remote processing devices geographically remote from said wearer, said remote memory configured to store previously acquired measurements of said pulse rate, at least some of said previously acquired measurements comprising generalized measurements not specifically associated with said wearer, said one or more remote processing devices configured to compare with said at least one remote processor said measurements with said previously acquired measurements, and to determine using said at least one remote processor said wearer-specific calibration data when said comparing calibrates said measurements to said previously acquired measurements, said wearer-specific calibration information including relationships between noninvasive measurements and clinically-determined output measurements of one or more physiological parameters, said local processing device configured to receive said wearer-specific calibration information from said remote processing device and configured to determine with said at least one local processor wearer-specific calibrated measurements responsive to additional out measurement signals from said noninvasive sensor; and said display providing display indicia to said wearer, said indicia responsive to said wearer-specific calibrated measurements values of said pulse rate.

14. The monitoring system of claim 13, wherein said noninvasive sensor comprises a blood oxygen saturation sensor.

15. The monitoring system of claim 13, wherein said one or more remote processing devises operably communicate through at least a cloud network.

16. The monitoring system of claim 13, wherein said local processing device recalibrates said patient-specific calibration data.

* * * * *